US008614305B2

(12) United States Patent
Hofmann et al.

(10) Patent No.: US 8,614,305 B2
(45) Date of Patent: Dec. 24, 2013

(54) NONVIRAL GENE DELIVERY VECTOR IOPAMIDOL, PROTAMINE, ETHIODIZED OIL REAGENT (VIPER)

(75) Inventors: Lawrence V. Hofmann, Los Altos, CA (US); Gloria L. Hwang, Hillsborough, CA (US); Luke J Higgins, Ellicott City, MD (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/583,872

(22) PCT Filed: Mar. 11, 2011

(86) PCT No.: PCT/US2011/028047
§ 371 (c)(1),
(2), (4) Date: Sep. 10, 2012

(87) PCT Pub. No.: WO2011/112902
PCT Pub. Date: Sep. 15, 2011

(65) Prior Publication Data
US 2013/0131154 A1   May 23, 2013

Related U.S. Application Data

(60) Provisional application No. 61/340,052, filed on Mar. 12, 2010.

(51) Int. Cl.
C12N 15/11   (2006.01)
A61K 48/00   (2006.01)
C07H 21/02   (2006.01)
C07H 21/04   (2006.01)

(52) U.S. Cl.
USPC .................. 536/23.1; 536/24.5; 514/44

(58) Field of Classification Search
USPC ............................ 514/44; 536/24.5
See application file for complete search history.

(56) References Cited

U.S. PATENT DOCUMENTS 5,744,166 A   4/1998   Illum

OTHER PUBLICATIONS

Song et al. (Nature Biotechnology, 2005 vol. 23:709-719).*
Higgins et al. (Abstract No. 368: In Vitro Transfection of Hepatoma Cells and Hepatocytes with a Nonviral Vector Using Protamine and Ethiodol. Journal of Vascular and Interventional Radiology. Feb. 2008 (vol. 19, Issue 2, p. S135).*
Higgins et al. (J Vasc Interv Radiol, 2011, vol. 22:1457-1463).*
Kim et al. "Intraarterial Gene Delivery in Rabbit Hepatic Tumors: Transfection with Nonviral Vector by Using Iodized Oil Emulsion". Radiology, Sep. 2006, vol. 240, No. 3, pp. 771-777.
Li et al. "Gene therapy progress and prospects: non-viral gene therapy by systemic delivery". Gene Ther., Sep. 2006, vol. 13, No. 18, pp. 1313-1319.
Brewer et al. "Protamine-induced condensation and decondensation of the same DNA molecule". Science, Oct. 1999, vol. 286, No. 5437, pp. 120-123.
Hunter "Molecular hurdles in polyfectin design and mechanistic background to polycation induced cytotoxicity". Adv Drug Deliv Rev, Dec. 2006, vol. 58, No. 14, pp. 1523-1531.
Sorgi et al. "Protamine sulfate enhances lipid-mediated gene transfer". Gene Ther., Sep. 1997, vol. 4, No. 9, pp. 961-968.

(Continued)

Primary Examiner — Terra Cotta Gibbs
(74) Attorney, Agent, or Firm — Jenny Buchbinder

(57) ABSTRACT

Embodiments are related to nonviral gene delivery vectors using only FDA-approved components: iopamidol, protamine, and ethiodized oil.

19 Claims, 12 Drawing Sheets

(56) References Cited

OTHER PUBLICATIONS

Collins et al. "Nuclear localisation and pDNA condensation in non-viral gene delivery". J Gene Med, Apr. 2007, vol. 9, No. 4, pp. 265-274.

Aoki et al. "Polyethylenimine-mediated gene transfer into pancreatic tumor dissemination in the murine peritoneal cavity". Gene Ther, 2001, vol. 8, pp. 508-514.

PCT/US2011/028047 International Search Report.

* cited by examiner

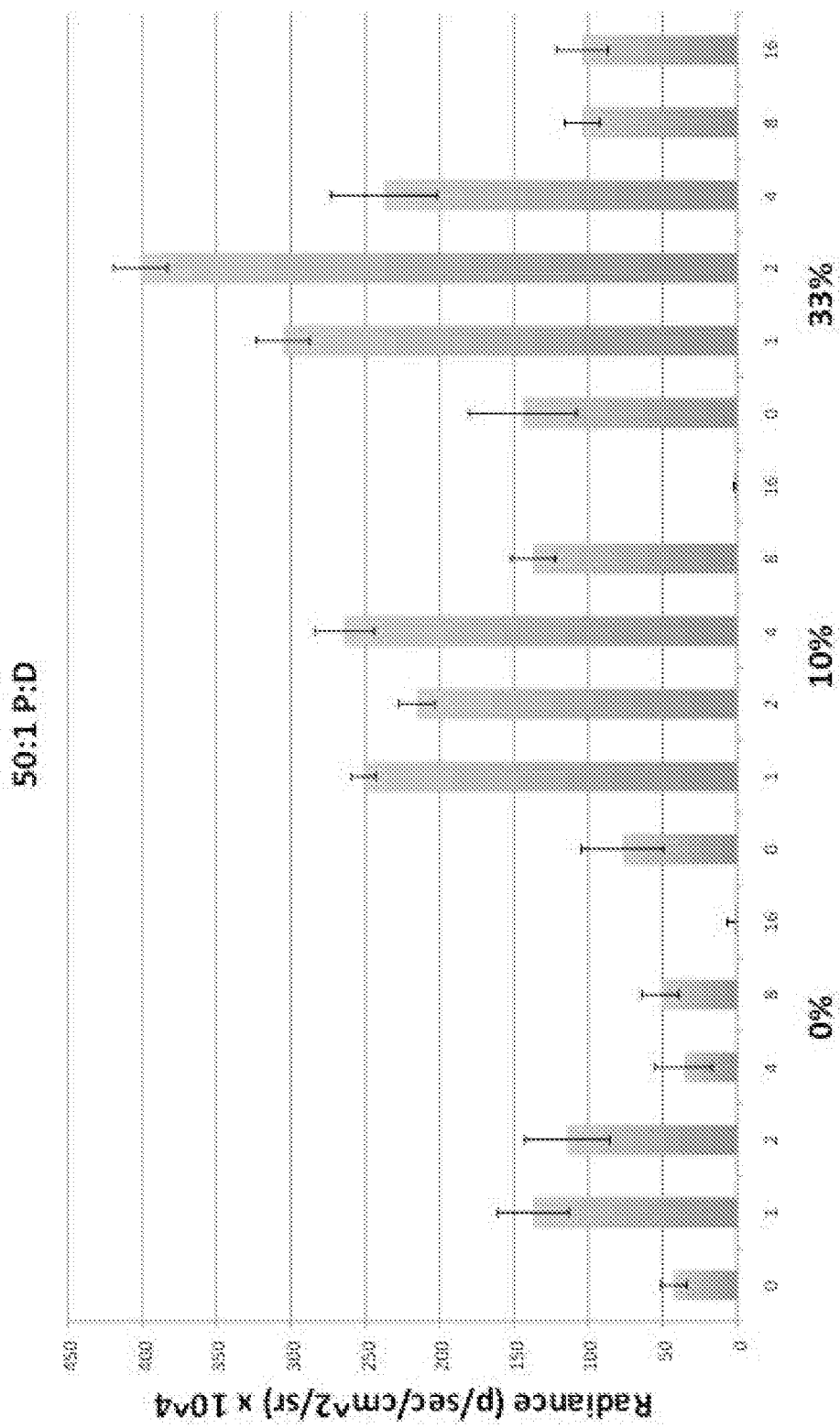

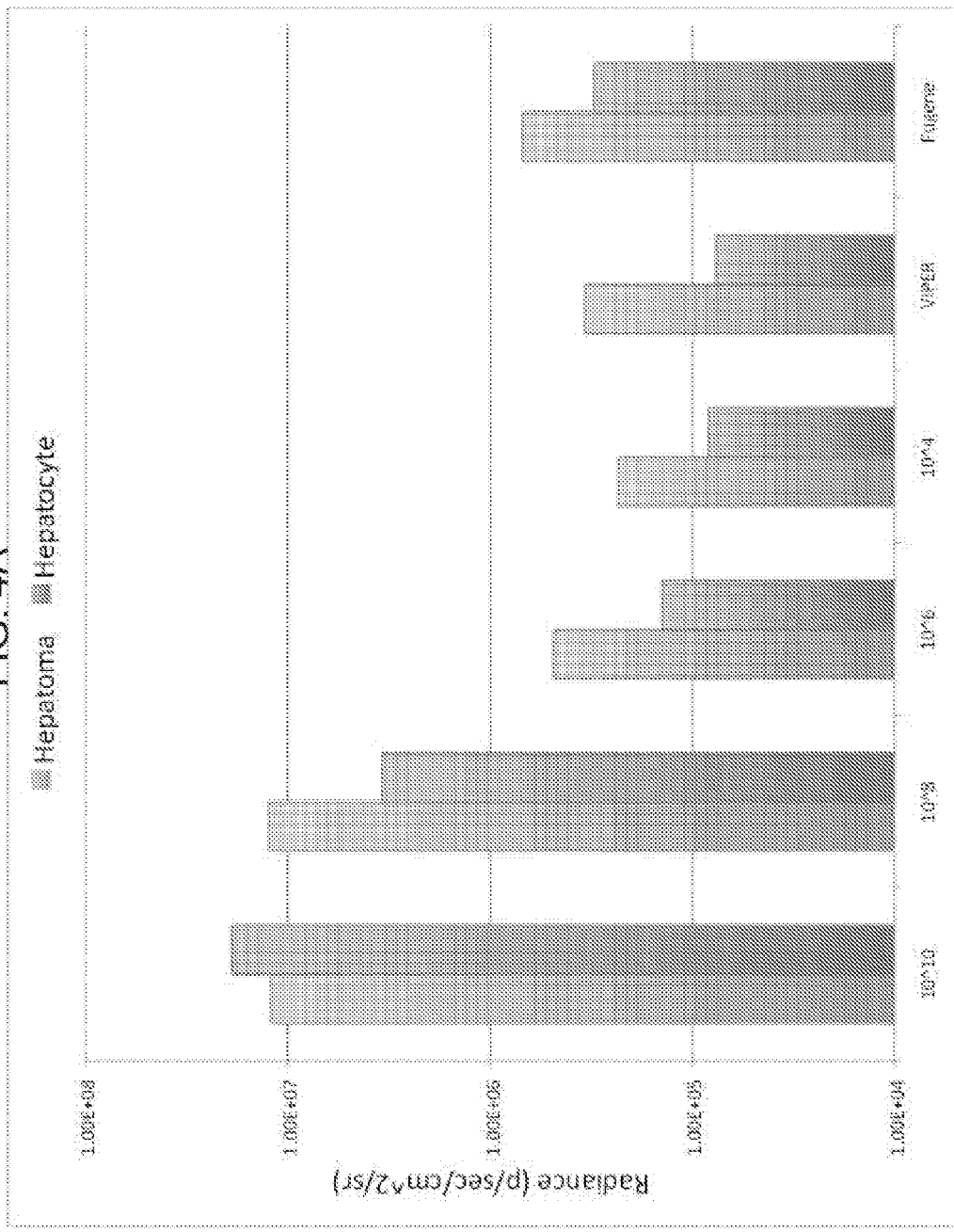

NONVIRAL GENE DELIVERY VECTOR IOPAMIDOL, PROTAMINE, ETHIODIZED OIL REAGENT (VIPER)

CROSS-REFERENCE TO RELATED APPLICATIONS

This application claims the benefit of U.S. Provisional Application No. 61/340,052, filed Mar. 12, 2010, which is incorporated herein by reference; furthermore, this application claims priority as the national stage application of PCT/US2011/028047, having an international filing date of Mar. 11, 2011, which is hereby incorporated in its entirety.

BACKGROUND OF THE INVENTION

1. Field of the Invention

The field of the invention is bio-affecting and body treating compositions of iopamidol, protamine, and ethiodized oil.

2. Description of Related Art

Hepatocellular carcinoma (HCC) has become increasingly prevalent in the United States (Altekruse S F et al., J Clin Oncol 2007, 27, 1485-91; El-Serag H B et al., Arch Intern Med 2007, 167, 1983-9). Systemic treatments for HCC have limited efficacy and inherent toxicity (Worns M A et al., Dig Dis 2009, 27, 175-88). In contrast, the use of chemoembolization (Brown D B et al., J Vasc Intery Radiol 2009, 20, S425-34) to treat HCC allows for localized, concentrated delivery of chemotherapeutic agents resulting in less systemic toxicity, improved quality of life, and significant prolongation of survival (Lau W Y, Lai E C, Hepatobiliary Pancreat Dis Int 2008, 7, 237-57). However, the benefits of chemoembolization may be less dramatic in patients with advanced disease (large, multifocal, and/or infiltrative tumor, vascular invasion, severe cirrhosis) (Kothary N et al., J Vasc Intery Radiol 2007, 18, 1517-26) and new treatment strategies are being actively pursued.

Over decades of trial and error, chemoembolization has been iteratively improved for localized delivery to the tumor site incorporating cytotoxic chemotherapeutic agents, a lipid component to enhance tumor uptake, a contrast agent for fluoroscopic visualization, and embolic material to impede washout and induce ischemia. The chemoembolization strategy is suited to treat HCC given the arterial blood supply to tumors and the inherent avidity of HCC for ethiodized oil (Bruix J et al., Gastroenterology 2004, 127, S179-88, Maleux G et al., Dig Dis 2009, 27, 157-63). In vitro studies, including electron microscopy analysis, have shown that emulsified ethiodized oil droplets are taken up by hepatoma cells via endocytosis, a process that is more active in these cells than in hepatocytes (Chou F I et al., Nucl Med Biol 1995, 22, 379-86). The viscosity of the ethiodized oil emulsion also allows it to act as an embolic agent, reducing blood flow to the tumor and decreasing washout of the chemotherapeutic agents. This increases the intratumoral area under curve (AUC) while decreasing the systemic exposure to the chemotherapeutic agents (Lau W Y, Lai E C, Hepatobiliary Pancreat Dis Int 2008, 7, 237-57).

In addition to chemoembolization, researchers have explored the use of gene therapy as an HCC treatment strategy. Delivery of thymidine kinase, tumor suppressor genes, and anti-angiogenesis genes into tumor cells would afford improved drug selectivity and possibly tumor growth attenuation (Mohr L et al., Expert Opin Biol Ther 2002, 2, 163-75; Peñuelas I et al., Gastroenterology 2005, 128, 1787-95). Although there are a number of genes with oncocidal activity, the difficult problem of achieving efficient gene delivery while maintaining acceptable indices of toxicity remains a challenge. Both viral and nonviral gene delivery vectors have been developed with viral vectors being more efficient gene carries (Boeckle S, Wagner E, AAPS J 2006, 8, E731-42). Unfortunately, the host's immune response limits both the safety and efficacy of viral vectors (Boeckle S, Wagner E, AAPS J 2006, 8, E731-42; Descamps D, Benihoud K, Curr Gene Ther 2009, 9, 115-27; Massari I et al., Exp Gerontol 2002, 37, 823-31). In the context of HCC, animal studies have shown the utility of combining chemoembolization and transarterial nonviral gene therapy strategies. Kim et al. demonstrated that an emulsion of ethiodized oil, an aqueous contrast agent, and condensed polyethyleneimine:DNA particles could deliver plasmid DNA to VX2 liver tumors in a rabbit model (Kim Y I et al., Radiology 2006, 240, 771-7). Although gene transfection was significant, polyethyleneimine has a prohibitive toxicity profile, making clinical translation difficult (Hunter A C, Adv Drug Deliv Rev 2006, 58, 1523-31).

SEGUE TO THE INVENTION

In order to address the toxicity concerns of using existing nonviral vectors, we present the development of a nonviral vector using only FDA approved components. In addition, we compare this nonviral vector to both the most commonly used nonviral vector for in vitro studies, the cationic lipid Fugene (Roche, Indianapolis, Ind.), and the most commonly used viral vector for gene therapy, adenovirus.

BRIEF SUMMARY OF THE INVENTION

A first embodiment is a nonviral gene delivery vector comprising iopamidol, protamine, and ethiodized oil.

A second embodiment is a drug product comprising a nonviral gene delivery vector consisting of plasmid DNA, iopamidol, protamine, and ethiodized oil.

A third embodiment is the vector of the first embodiment further comprising plasmid DNA.

A fourth embodiment is the vector of the first embodiment further comprising short interfering RNAs (siRNAs), microRNAs (miRNAs), antisense oligonucleotides (ASO), ribozymes, or triplex-forming oligonucleotides.

A fifth embodiment is the vector of the second or third embodiment, wherein the protamine and DNA form a complex having a protamine to DNA mass ratio of between 1:1 to 1000:1.

A sixth embodiment is the vector of the second, third, or fifth embodiment, wherein the protamine and DNA form a complex having a protamine to DNA mass ratio of 20:1, 50:1, 100:1, or 200:1.

A seventh embodiment is the vector of the second, third, fifth, or sixth embodiment, wherein the concentration of iopamidol is between 1% and 100%.

An eighth embodiment is the vector of the second, third, fifth, sixth, or seventh embodiment, wherein the concentration of iopamidol is 10% or 33%.

A ninth embodiment is the vector of the second, third, fifth, sixth, seventh, or eighth embodiment, wherein the concentration of ethiodized oil is between 1% and 100%.

A tenth embodiment is the vector of the second, third, fifth, sixth, seventh, eighth, or ninth embodiment, wherein the concentration of ethiodized oil is 1%, 2%, 4%, 8%, or 16%.

An eleventh embodiment is the vector of the second, third, fifth, sixth, seventh, eighth, ninth or tenth embodiment, wherein the amount of plasmid DNA is between 1 ng and 4000 ng.

A twelfth embodiment is the vector of the second, third, fifth, sixth, seventh, eighth, ninth, tenth, or eleventh embodiment, wherein the amount of plasmid DNA is 200 ng.

A thirteenth embodiment is the vector of the second, third, fifth, sixth, seventh, eighth, ninth, tenth, eleventh, or twelfth embodiment, wherein the plasmid DNA comprises a tumor suppressor gene, encodes a tumor-specific antigen, encodes an enzyme capable of converting a prodrug to a cytotoxic drug, comprises a cytotoxic or pro-apoptotic gene, encodes a cytokine, encodes an anti-angiogenic factor, encodes UGT1A1, encodes ornithine transcarbamylase, encodes factor VIII, encodes factor IX, or comprises a combination of the Neurod and Btc genes.

A fourteenth embodiment is a process for transfecting mammalian cells comprising administering the vector of any of the first to thirteenth embodiment to mammalian cells in an amount effective to transfect the cells.

A fifteenth embodiment is the process of the fourteenth embodiment, wherein delivery of the vector is in vivo.

A sixteenth embodiment is the process of the fourteenth embodiment, wherein delivery of the vector is in vitro or ex vivo.

A seventeenth embodiment is the process of the fourteenth, fifteenth, or sixteenth embodiment, wherein in vivo or ex vivo delivery is systemic.

An eighteenth embodiment is the process of the fourteenth, fifteenth, or sixteenth embodiment, wherein in vivo or ex vivo delivery is local.

A nineteenth embodiment is the process of the fourteenth, fifteenth, sixteenth, seventeenth, or eighteenth embodiment, wherein the cells are hepatoma cells.

A twentieth embodiment is a process for making a nonviral gene delivery vector comprising mixing a DNA stock solution with a protamine solution, adding iopamidol, and adding ethiodized oil in amounts effective to make a nonviral gene delivery vector.

DETAILED DESCRIPTION OF THE EMBODIMENTS

Figure 1:
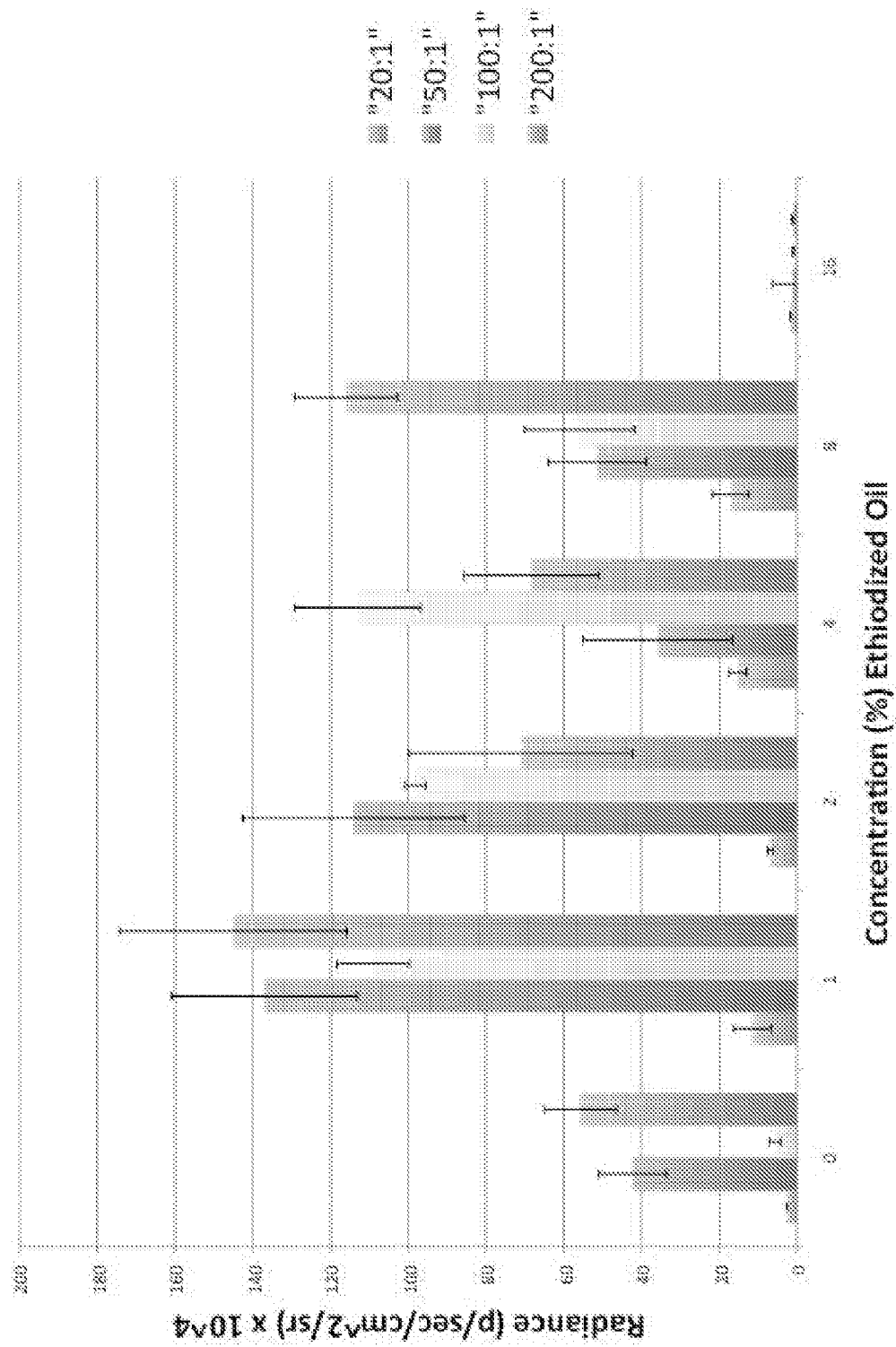
FIG. 1. Characterizing the effect of Protamine:DNA mass ratio variation on transfection efficiency. P:D ratios (20:1-light gray, 50:1-dark grey, 100:1-off white, and 200:1-blackish) were measured with varied ethiodized oil concentrations (1, 2, 4, 8, and 16%). Y-axis: Radiance (p/sec/cm^2/sr). X-axis: % ethiodized oil. Error bars denote standard error of the mean.
Figure 2B:
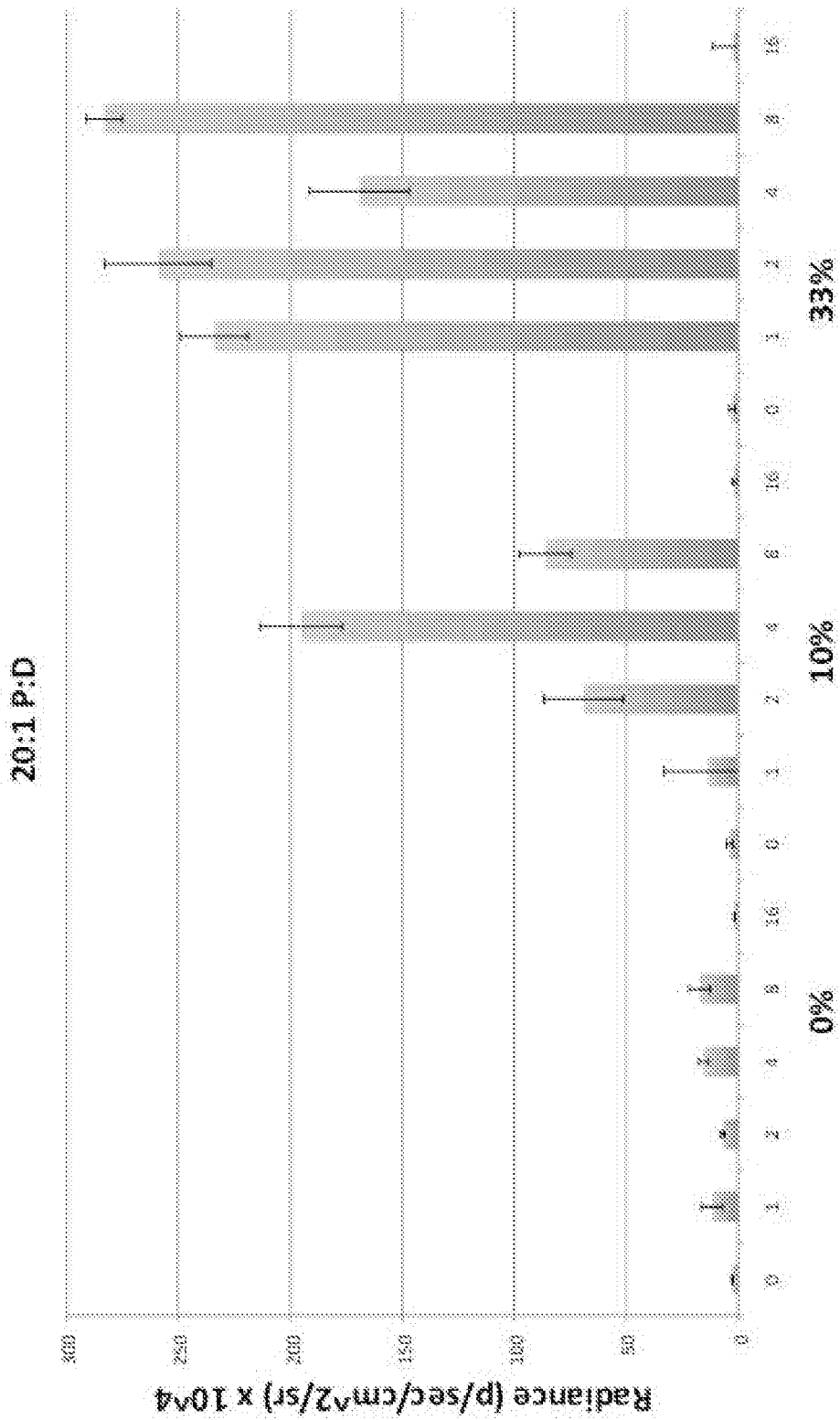
FIG. 2. Characterization of varying iopamidol and ethiodized oil concentration on transfection efficiency. Constant P:D mass ratios were used: 20:1 (A), 50:1 (B), 100:1 (C), and 200:1 (D). Y-axis: Bioluminescence radiance (p/sec/cm^2/sr×10^4). X-axis: Ethiodized oil concentrations (0, 1, 2, 8, 16%) at three iopamidol concentrations (0, 33, 100%). Error bars denote standard error of the mean.
Figure 2C:
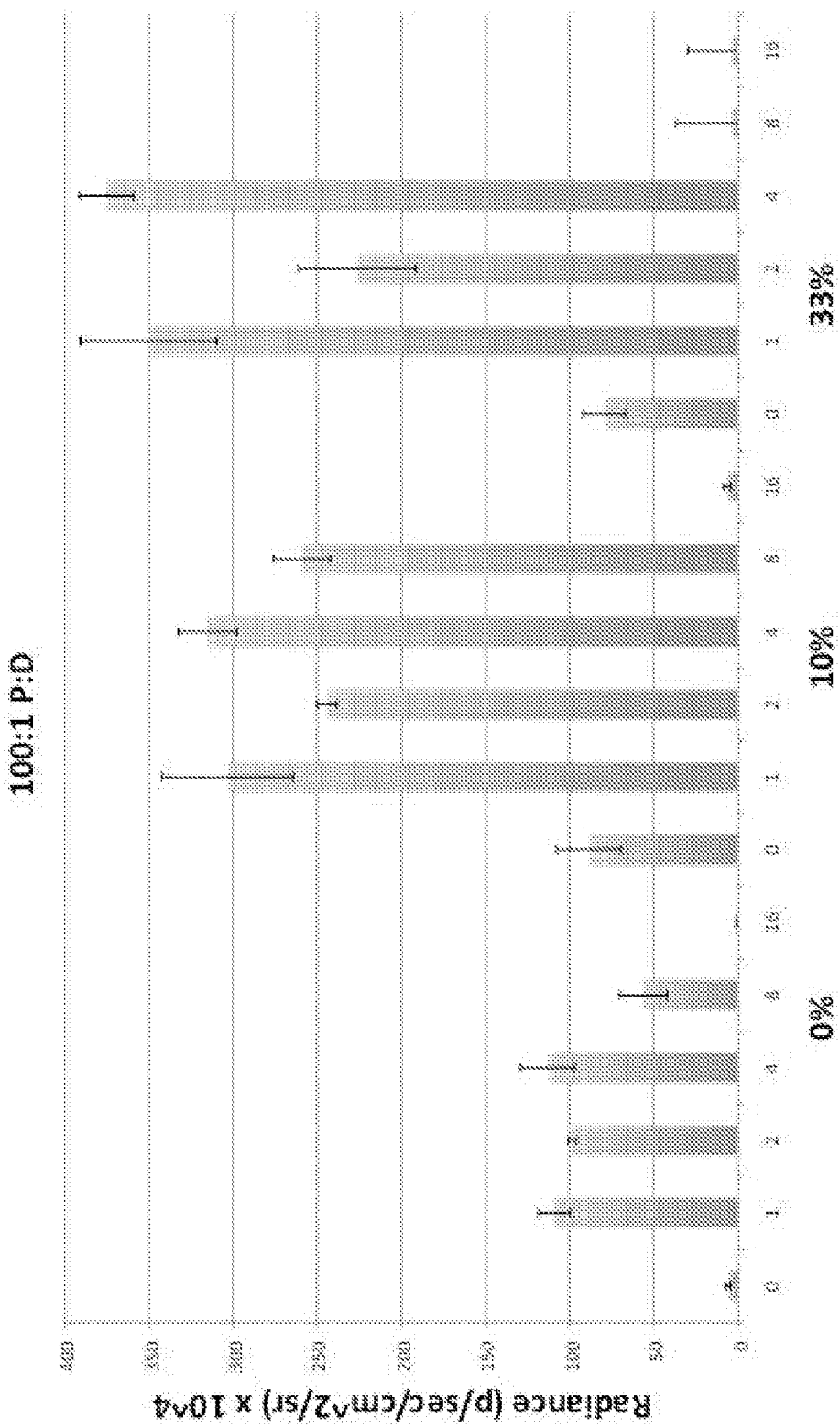
Figure 2D:
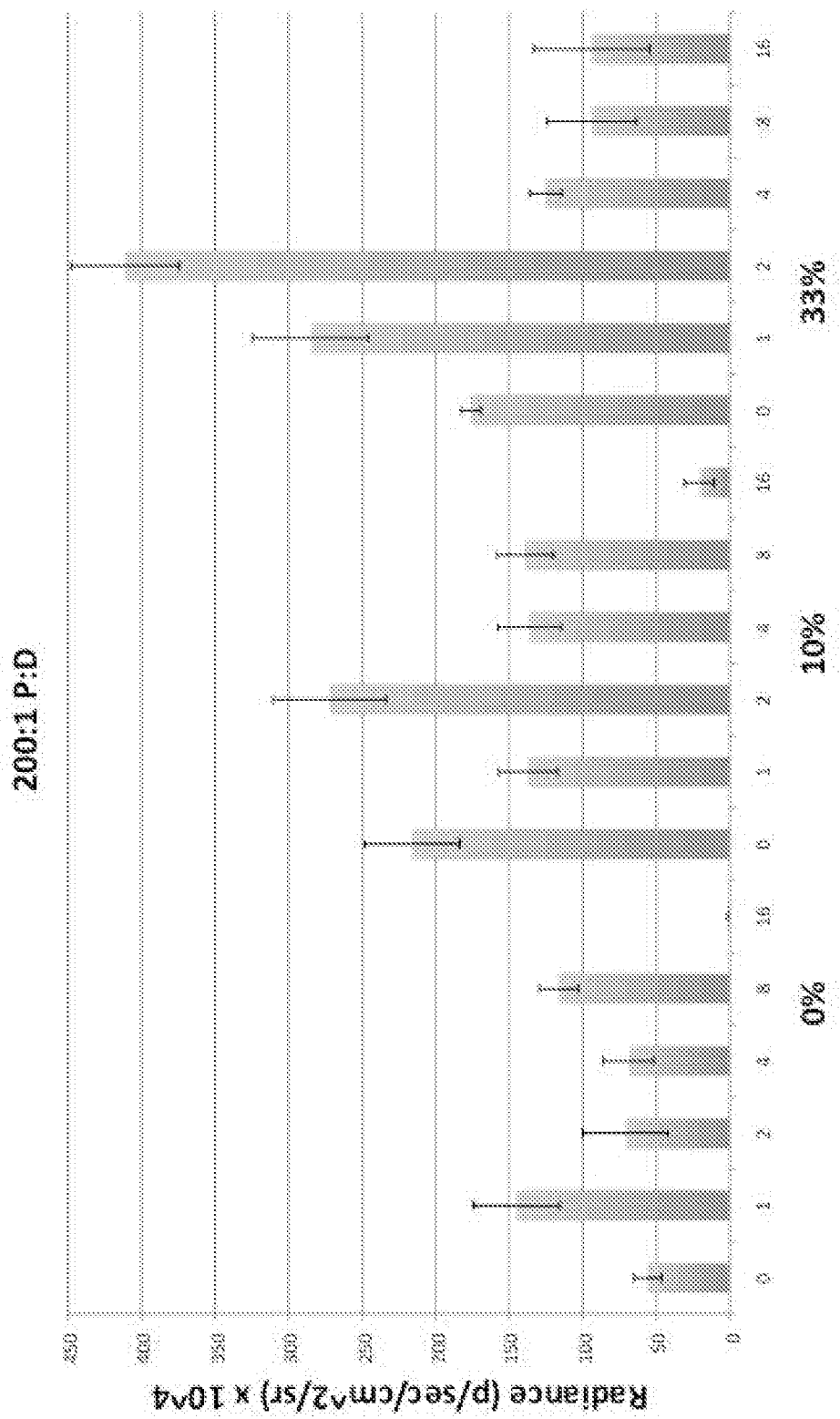

Briefly, our purpose was to develop a nonviral vector using only FDA-approved components: iopamidol, protamine, and ethiodized oil. Rat hepatocellular carcinoma cells were transfected in triplicate under varying conditions using firefly luciferase as a reporter gene. Conditions included variations of a protamine: DNA complex (20:1, 50:1, 100:1, 200:1 mass ratios), iopamidol (0%, 10%, 33%, 75%, 100%), and ethiodized oil (0%, 1%, 2%, 4%, 8%, and 16%). The conditions affording efficient gene transfer and ease of translation to in vivo studies were selected for cell line comparison (hepatocellular carcinoma cells versus hepatocytes). Adenoviral transduction was compared to nonviral vector transfection. At low concentrations, ethiodized oil increased transfection efficiency regardless of protamine:DNA mass ratio. However, high concentrations resulted in significant attenuation. Unexpectedly, the addition of iopamidol to protamine: DNA complexes markedly improved transfection efficiency. Using an optimal protamine:DNA, iopamidol, and ethiodized oil solution, DNA transfection of normal liver and tumor cells showed significant selectivity for tumor cells. Transfection efficiency using the nonviral vector was comparable to 10^4 pfu adenovirus. The development of the VIPER system provides an alternative to viral gene therapy using FDA-approved components.

Definitions

Unless defined otherwise, terms used herein have the same meaning as commonly understood by one of ordinary skill in the art to which this invention belongs. E.g., Paul Singleton and Diana Sainsbury, *Dictionary of Microbiology and Molecular Biology* (3d ed. revised, John Wiley & Sons, Chichester, England, 2006).

Iopamidol is a nonionic contrast agent (Bonati F et al., Invest Radiol 1980, 15, S310-6) that derives its radiopaque property from a triiodinated benzene ring, and its water solubility from three highly hydrophilic groups attached to the benzene ring (Pitrè D, Felder E, Invest Radiol 1980, 15, S301-9). It is commercially available from Bracco, Princeton, N.J. Some pharmacokinetics and safety information is published as Thompson, W M et al., AJR Am J Roentgenol 1984, 142, 329-32 and Bourin, M et al., Clin Pharmacokinet 1997, 32, 180-93.

Protamine has been shown to be able to condense plasmid DNA efficiently for delivery into several different types of cells, with protamine sulfate being superior to the other salt forms of the protamines (Sorgi, F L et al., Gene Ther 1997, 4, 961-8). Protamine has been confirmed to condense DNA into toroid-like structures (Brewer, L R et al., Science 1999, 286, 120-3). Protamines tend to be purified from the testes of fish, usually salmon (Package insert, APP Pharmaceuticals, Schaumburg, Ill.). The true protamines are typically short proteins (50-110 amino acids) that can contain up to 70% arginine (Balhorn, R, Genome Biol 2007, 8, 227). Gene and protein sequences have been determined for protamines from more than 100 vertebrate species (id.). The structural element that has been identified in all vertebrate protamines is a series of small "anchoring" domains containing multiple arginine or lysine amino acids that are used to bind the protein to DNA (id.).

Ethiodized oil, also known as lipiodol, is composed of ethyl esters of iodized fatty acids of poppy seed oil and has the advantage of being radiopaque and therefore useful as a contrast agent (Package insert, Guerbet, Roissy, France). Iodized oil administered via the hepatic artery localizes selectively in hepatocellular carcinomas (HCCs) and has been used as a vehicle for cytotoxic agents (Bhattacharya, S et al., Br J Surg 1994, 81, 1563-71). Retention in HCCs is explained by pinocytosis into tumor cells and endothelial cells (Bhattacharya, S. et al., Br J Cancer 1996, 73, 877-81).

The term "drug" means, as stated in the Federal Food, Drug, and Cosmetic Act, an article intended for use in the diagnosis, cure, mitigation, treatment, or prevention of disease in man or other animal. The term "biologic" means, as defined by the Food and Drug Administration, a subset of drugs that are distinguished by the biological manufacturing process. These definitions serve to differentiate a drug substance from a drug product. A drug product is the finished form, e.g., a parenteral drug product containing the drug substance. Efficacy studies are done to provide evidence of a drug's ability in diagnosis, cure, mitigation, treatment, or prevention of a disease. Diagnosis, cure, mitigation, treatment, or prevention does not mean 100% efficacy. Rather, diagnosis, cure, mitigation, treatment, or prevention means some level of efficacy, anywhere from 1% to 100%.

Vector-Iopamidol-Protamine-Ethiodized Oil Reagent (VIPER)

Gene therapy holds great potential as a future treatment for hepatocellular carcinoma especially given the plethora of molecular imaging reporter and therapeutic genes. Unfortunately, engineering an efficient non-toxic gene delivery system has remained elusive. Although viral vectors are relatively efficient gene delivery agents, toxicity concerns limit translation to the clinic, particularly in patients with poor liver function (Boeckle S, Wagner E, AAPS J 2006, 8, E731-42; Descamps D, Benihoud K, Curr Gene Ther 2009, 9, 115-27; Massari I et al., Exp Gerontol 2002, 37, 823-31). While polyethyleneimine remains a viable agent for in vitro and in vivo studies it is unlikely to be clinically viable given its narrow therapeutic index (Hunter A C, Adv Drug Deliv Rev 2006, 58, 1523-31). Therefore, developing and characterizing the vector-iopamidol-protamine-ethiodized oil reagents (VIPER) nonviral vector system with FDA-approved components, albeit for a new therapeutic indication, provides a safe and efficacious alternative.

Figure 5:
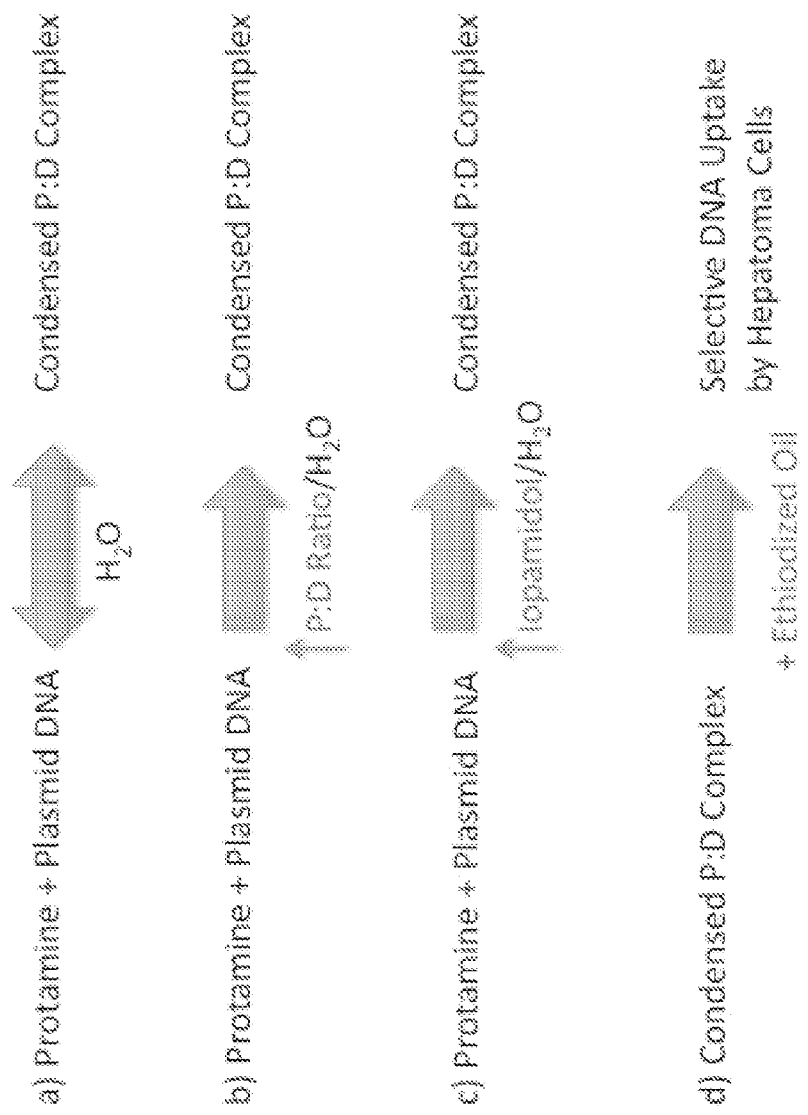
FIG. 5. Thermodynamic rationale for the design of the VIPER system. a) In water only, the reaction is in equilibrium. b) Increasing the amount of protamine relative to DNA, drives the equation to the right. c) By adding and increasing the amount of iopamidol, the hydrophobicity of the transfection solution was increased. This favors charge neutralization and drives the equation to the right. d) The addition of ethiodized oil facilitates selective uptake by hepatoma cells. The Protamine:DNA mass ratio is denoted by P:D.

The design of the VIPER nonviral system required the characterization of four variables: protamine, plasmid DNA, ethiodized oil, and iopamidol (FIG. 5). Protamine serves as a DNA-condensing agent providing protection against degradation, facilitating protamine:DNA (P:D) particle size sufficient for cellular uptake, and the primary sequence of protamine provides a mechanism for cell entry. Iopamidol is required for visualization of gene delivery when translated to the interventional suite. Ethiodized oil, also radiopaque, provides selectivity for tumor uptake as exemplified by the efficacy of chemoembolization. Furthermore, each component facilitates ultimate translation to the clinic (see Table).

The first step in VIPER design was the characterization of varied P:D molar ratios. Protamine is FDA-approved for the immediate inactivation of heparin activity. The mechanism of action in this context relies upon the interaction of the polycationic protamine molecule and the polyanionic heparin molecule (Rossmann P et al., Virchows Arch B Cell Pathol Incl Mol Pathol 1982, 40, 81-98). In nature, protamine is a DNA-condensing agent allowing for efficient packaging within sperm cell nuclei, also governed by electrostatic complementarity (Balhorn R, Genome Biol 2007, 8, 227). This latter function has lead to studies utilizing protamine as a nonviral vector for gene delivery (Kharidia R et al., Biochemistry (Mosc) 2008, 73, 1162-8). In addition to the electrostatic complementarity with DNA, protamine is a cell penetrating polypeptide. The protamine amino acid sequence is rich in arginine residues that contain guanidinium functional groups, the active moieties facilitating cell entry (Laufer S D, Restle T, Curr Pharm Des 2008, 14, 3637-55; Maitani Y, Hattori Y, Expert Opin Drug Deliv 2009, 6, 1065-77; Rothbard J B et al., J Am Chem Soc 2004, 126, 9506-7). Thus, the combination of the electrostatic interactions and the cell-penetrating properties of protamine allow for DNA transfection, albeit with poor efficiency when used alone.

Unexpectedly, the concentration of iopamidol in the absence of ethiodized oil affected the transfection efficiency of the P:D complexes (FIG. 2A-D). Transfection efficiency markedly improved with the addition of 10% or 33% iopamidol to 20:1 P:D ($p<0.001$). It is possible that the contrast agent initially improved DNA condensation by increasing the hydrophobicity of the transfection solution favoring charge neutralization and P:D complex formation (Ewert K et al., Curr Med Chem 2004 11, 133-49; Wong F M et al, Biochemistry 1996, 35, 5756-63). Charge neutralization via complex formation would be thermodynamically favored in an organic solution (i.e., iopamidol) (Dizhe E B et al., Biochemistry (Mosc) 2006, 71, 1350-6; Norberg J, Arch Biochem Biophys 2003, 410, 48-68). It is not illogical then that the 20:1 P:D condition, having the least favorable equilibrium relative to other conditions based on Le Chatelier's principle, gave the most marked improvement in transfection efficiency. Other studies have shown that transfection efficiency using DNA condensing agents is directly proportional to the extent of complex formation and the size of the complex particles (Kharidia R et al., Biochemistry (Mosc) 2008, 73, 1162-8; Davis M E, Curr Opin Biotechnol 2002, 13, 128-31).

In accord with our past experience, we found that the addition of ethiodized oil (1-2%) to the P:D complex initially improved transfection efficiency while a concentration of 16% gave markedly decreased transfection. This in vitro observation is unique. Interestingly, the polyethyleneimine-ethiodized oil vector described by Kim et al. used one-third final volume ethiodized oil, a concentration that was toxic to hepatoma cells in vitro in our study, and only moderately effective for in vivo transfection (Kim Y I et al., Radiology 2006, 240, 771-7).

The initial improvement in transfection efficiency at 1-2% ethiodized oil is likely due to an inherent avidity of hepatoma cells for the oil as well as an increased metabolic activity. Although the precise mechanism of ethiodized oil is incompletely understood, the molecular constitution of the hepatoma cell surface is distinct from normal liver cells with unique surface proteins and glycosylation patterns (Chou F I et al., Nucl Med Biol 1995, 22, 379-86; Bhattacharya S et al., Br J Cancer 1996, 73, 877-81; Sudhakar C, Mangamoori L N, J Gastroenterol Hepatol 2008, 23 (7 Pt 2), e283-9). These properties probably contribute to the observed selectivity in tumor uptake.

Using the polyethyleneimine-ethiodized oil vector, Kim et al. showed that the addition of iopamidol to a mixture of oil and aqueous phases improved emulsification, putatively by matching the specific gravity of each phase (Kim Y I et al., Radiology 2006, 240, 771-7). In turn, the oil droplet sizes were considerably smaller, enhancing cellular uptake and gene delivery. The characterization of the VIPER system is consistent with this mechanism of gene delivery. The addition of 1% ethiodized oil to all P:D ratios improved transfection efficiency. This effect was markedly enhanced by the addition of iopamidol, possibly due to improved oil-in-water mixing.

Figure 3:
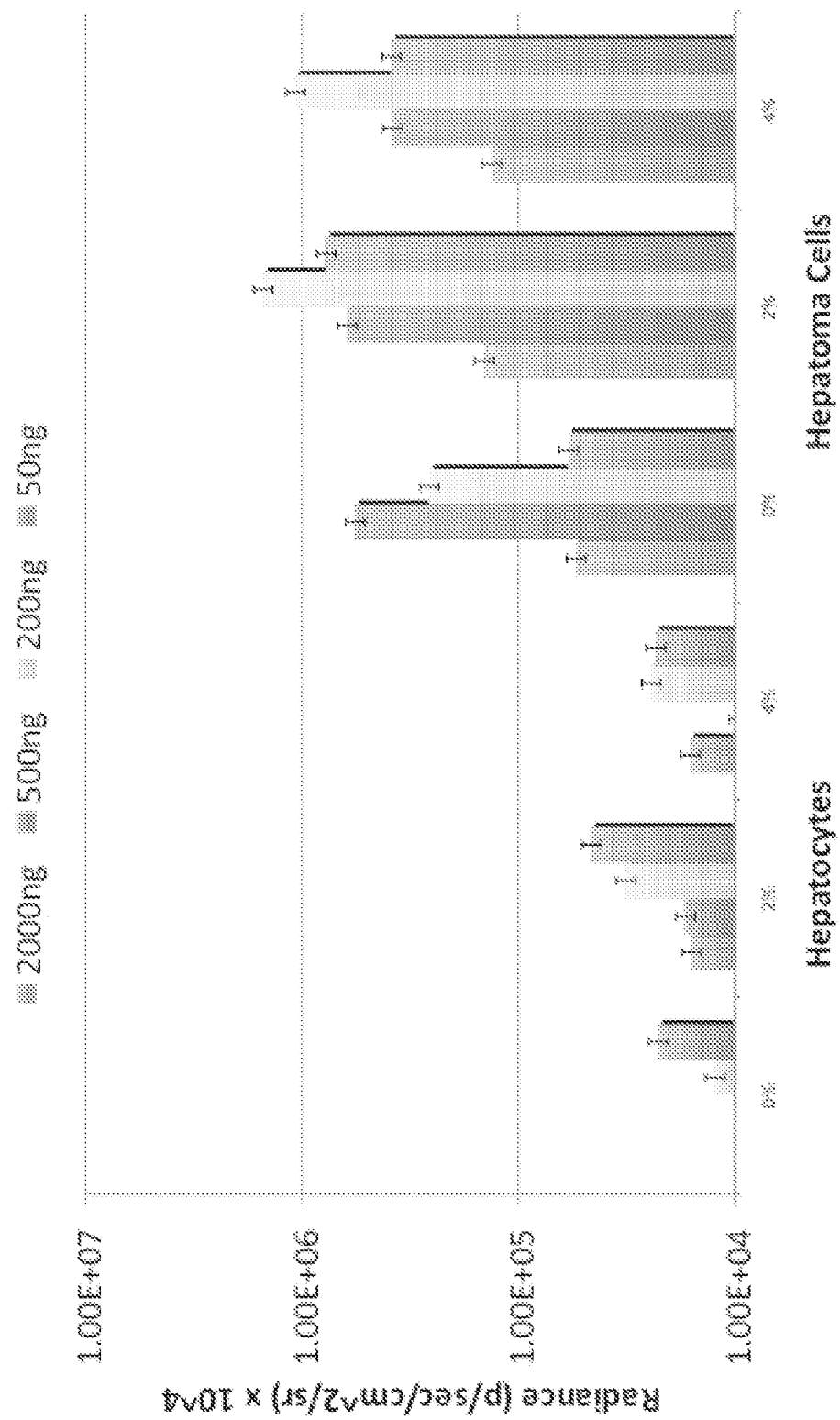
FIG. 3. VIPER transfection of hepatocytes compared with hepatoma cells. Varied amounts of DNA were tested (see graph legend) using 50:1 P:D, 33% iopamidol, and 0-4% ethiodized oil to transfect hepatocytes and hepatoma cells. The percent ethiodized oil (0, 2, 4%) is shown on the X-axis. Error bars denote standard error of the mean.
Figure 4B:
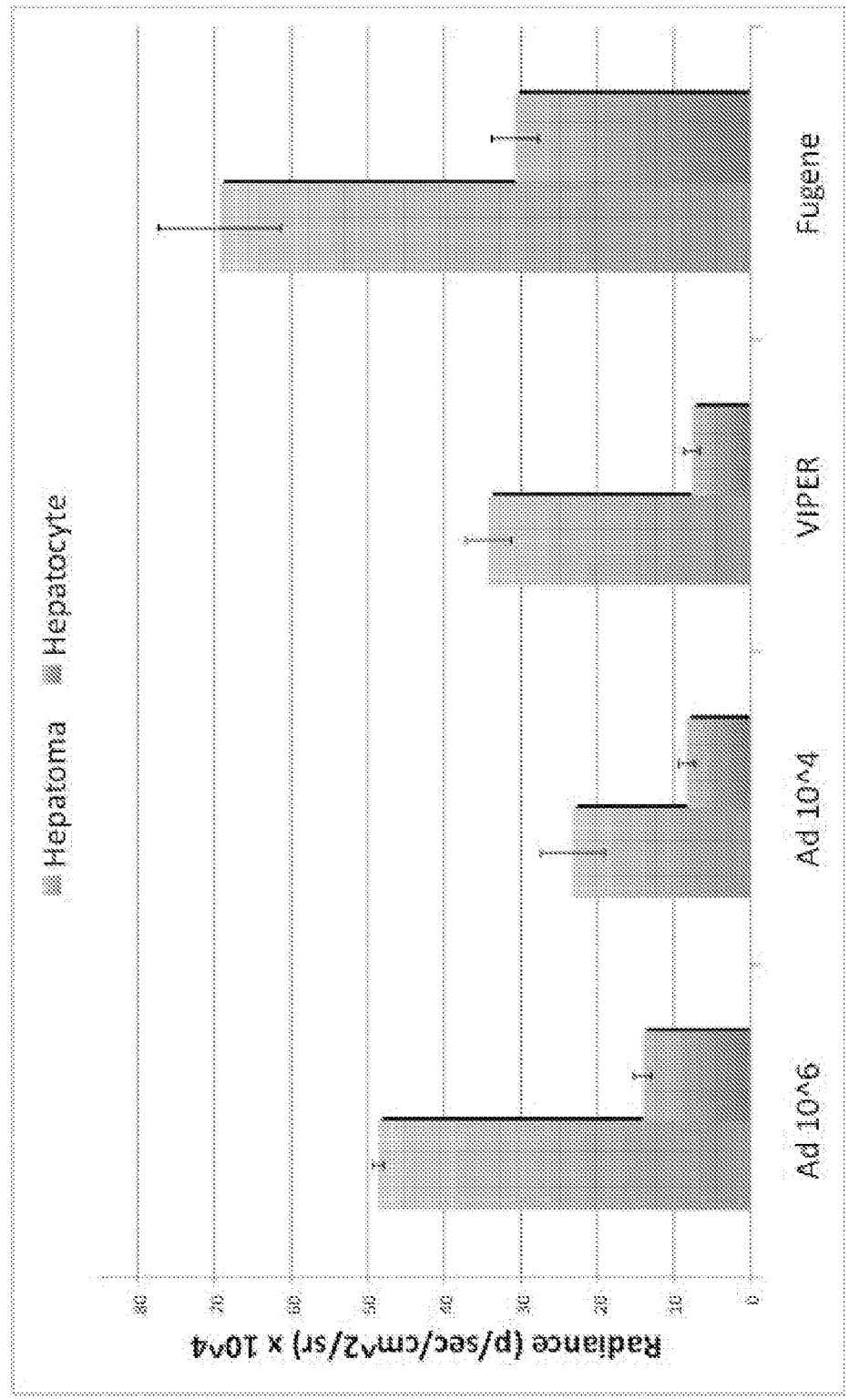
FIG. 4. Nonviral versus Viral Comparison. Hepatoma cells (light gray) and hepatocytes (dark grey) were transfected with the VIPER condition (200 ng DNA, 50:1 P:D, 33% iopamidol, 2% ethiodized oil) or the cationic lipid, Fugene (50 ng DNA). The nonviral transfection is compared to a titration of adenoviral DNA transduction using 10^10, 10^8, 10^6, or 10^4 pfu. Data is shown on a logarithmic scale (A). For closer comparison of comparable conditions, the data is shown as radiance×10^4. Error bars denote standard error of the mean (B). The ratio of transfection efficiency measured in hepatoma cells to that of hepatocytes illustrates the relative selectivity of viral and nonviral vectors (C).
Figure 4C:
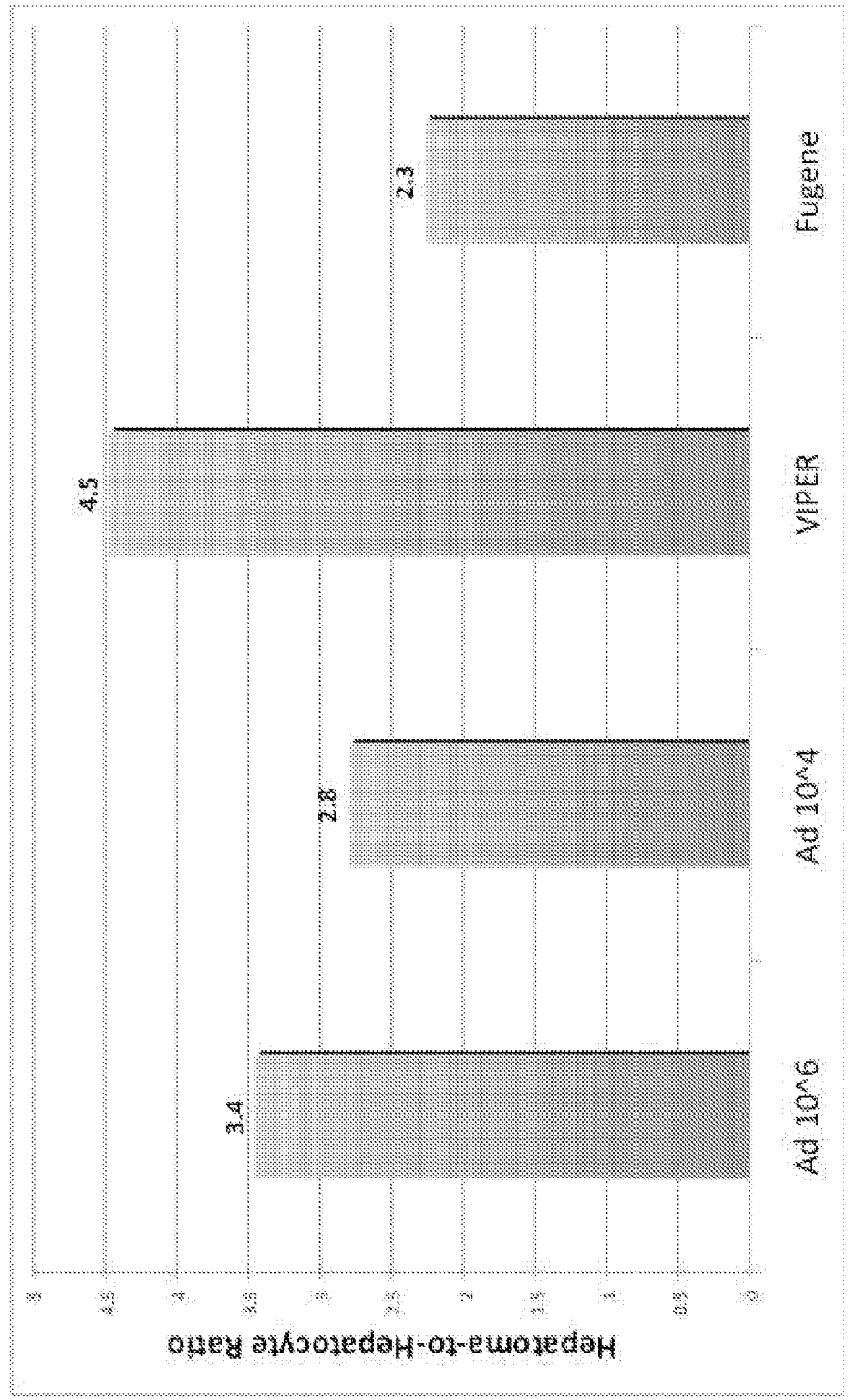

Clinically, the chemoembolization protocol, containing up to 50% ethiodized oil, affords hepatoma cell selective uptake of emulsified chemotherapeutic drugs, compared to hepatocytes (Bruix J et al., Gastroenterology 2004, 127, S179-88). The in vitro analysis of a relatively efficient VIPER condition (50:1 P:D, 33% iopamidol, and 2% ethiodized oil) is consistent with this observation as it is significantly more selective for hepatoma cells than hepatocytes (FIGS. 3 and 4C). In the chemoembolization protocol ethiodized oil facilitates selective tumor uptake by preferential accumulation and stagnation of chemotherapeutic agents within the tumor vasculature. However, in an in vitro context the mechanism of selectivity is apparently different. From a translational perspective tumor selectivity is desirable and can be enhanced with localized delivery using interventional techniques. And although the VIPER conditions are less efficient gene carriers than adenovirus, the nonviral vector is within 1.5 orders of magnitude of viral activity and is within an order of magnitude of Fugene activity (FIG. 4A,B), a cationic lipid commonly used for nonviral in vitro transfection but too toxic for clinical applications. Unlike the immunogenicity and toxicity of adenovirus, which limits iterative gene therapy treatments, the components of VIPER are significantly less toxic and less immunogenic. And with an iterative approach to gene delivery, the transfection efficiency of this nonviral system is expected to be within a range suitable for clinical translation.

In conclusion, the development of the VIPER system provides a viable alternative to viral gene therapy using FDA-approved components. At the interface of molecular imaging and interventional radiology, VIPER represents real-time visualization of gene delivery and subsequent therapeutic monitoring using existing techniques and molecular imaging reporters.

TABLE

VIPER - In vitro Mechanism of Action and Ultimate Applications in the Interventional Suite.

| Vector Component | In vitro Mechanism of Action | Clinical Translation |
|---|---|---|
| Iopamidol | Facilitates P:D complex formation Improves oil-in-water mixing | Fluoroscopic, real-time visualization |
| Protamine | DNA condensation Cell penetrating peptide | Relatively low toxicity and immunogenicity |
| Ethiodized Oil | Selective uptake by hepatoma cells | Arterial embolization |
| Reporter/ Therapeutic Gene | Variable (e.g., thymidine kinase reporter gene and gancyclovir therapy) | Therapeutic monitoring by positron emission tomography Differentiate responders from non-responders |

Study Results

Characterization of nonviral vector components. Characterization of plasmid DNA transfection efficiency of hepatoma cells using varied concentrations of P:D mass ratios and ethiodized oil is depicted in FIG. 1. P:D mass ratios 50:1, 100:1, and 200:1 gave higher transfection efficiency than 20:1 but these ratios did not differ significantly from each other ($p<0.001$ and $p<0.19$, respectively). Regardless of P:D mass ratio, an increase in ethiodized oil concentration from 0% to 1% resulted in an increase in transfection efficiency, with the most pronounced increase observed with the 100:1 P:D ratio and the least pronounced increase observed with the 20:1 P:D ratio ($p<0.001$). Increasing ethiodized oil concentration from 0% to 16% demonstrated signal increasing then decreasing ($p<0.001$).

Although the addition of ethiodized oil alone to the 20:1 P:D condition had little effect on transfection efficiency, the addition of 10% or 33% iopamidol to the aqueous phase of the 20:1 P:D nonviral vector gave more than one order-of-magnitude improvement in transfection efficiency (FIG. 2A) ($p<0.001$). Similar yet less dramatic improvement was observed as the concentration of iopamidol was increased while keeping P:D concentration constant at 50:1, 100:1, or 200:1 (FIG. 2B-C) ($p<0.001$). However, increasing iopamidol above 33% (50%, 75%, or 100%) decreased transfection efficiency regardless of P:D ratio or ethiodized oil concentration.

Selective transfection of hepatoma cells. With varying amounts of plasmid DNA (50 ng, 200 ng, 500 ng, and 2000 ng) and a VIPER condition (50:1 P:D, 33% iopamidol) with varied concentrations of ethiodized oil (0, 2, and 4%), DNA transfection of hepatocytes and hepatoma cells was compared. Maximal transfection was achieved using the optimized VIPER condition (50:1 P:D, 33% iopamidol, 2% ethiodized oil) with more than an order of magnitude selectivity for hepatoma cells compared to hepatocytes ($p<0.001$) (FIG. 3, 200 ng plasmid DNA).

Nonviral vector and viral vector comparison. Gene transduction with adenovirus (Ad5fLuc) was titrated by varying the multiplicity of infection (MOI) at 20000, 200, 2, and 0.2 corresponding to $10^{10}$, $10^8$, $10^6$, and $10^4$ plaque forming units (pfu). These values were compared to VIPER (200 ng DNA; 50:1 P:D, 33% iopamidol, 2% ethiodized oil). The efficiency of hepatoma cell transfection (average radiance) using VIPER was statistically comparable to that observed using $10^4$ pfu adenovirus and lower than $10^{10}$-$10^6$ pfu ($p<0.001$) (FIG. 4A-B). In hepatoma cells, adenoviral transfection efficiency plateaus at $10^7$ p/s/cem$^2$/sr, or approximately 20-times (1.3 orders of magnitude) more efficient than the nonviral vector (FIG. 4A). Using concentrations of viral particles that yield comparable transfection efficiency to that of VIPER ($10^4$ pfu), the VIPER condition is more selective for hepatoma cells (FIG. 4C) ($p<0.001$).

Nucleic Acid Based Therapeutics

The ability to control the gene expression of a desired cellular population via the delivery of nucleic acids has inspired applications in clinical and basic science. In the past, nonviral gene delivery referred to the delivery of plasmid DNA (pDNA) whereby the expression of a target protein would be increased. More recently, however, the term "gene delivery" has expanded to include the delivery of short interfering RNAs (siRNAs), microRNAs (miRNAs), antisense oligonucleotides (ASO), ribozymes, triplex-forming oligonucleotides, DNA-like peptide nucleic acids (PNAs), phosphorodiamidate morpholino oligonucleotides (PMOs), and modulators of alternative splicing, and the like, which can be used to inhibit the expression of a target protein.

Gene delivery employs both viral and nonviral vectors to deliver nucleic acids. Although viral delivery strategies are in general more efficient than their nonviral counterparts, an increasing concern about immune responses to viral vectors has motivated the development of nonviral delivery vectors that aim to synthetically mimic biologically produced viruses.

Strategies to administer nonviral delivery vectors in vivo can be divided into two main approaches: systemic delivery or direct delivery. Systemic delivery aims at engineering delivery vehicles that can be delivered non-invasively through a bodily fluid such as intravenously, transdermally, and orally, while targeting an appropriate tissue (e.g., tumor) or organ (e.g., liver). Local delivery, on the other hand, aims at bypassing the tissue-targeting step by delivering the nonviral vectors directly (or nearby) to the site of action, e.g., intrabiliary, intraparenchymal, intra-hepatic artery, intra-portal vein, intratumoral, and transvenous.

Gene Therapy for Cancer Disease

Thus far, most of the clinical trials in gene therapy have been aimed at the treatment of various types of cancer (66% of all gene therapy trials) (Edelstein M L et al., J Gene Med 2004, 6, 597-602). Gene therapy has been approved so far for the treatment of the following cancers: gynecological (breast, ovary, cervix), nervous system (glioblastoma, leptomeningeal carcinomatosis, glioma, astrocytoma, neuroblastoma), gastro-intestinal (colon, colorectal, liver metastases, post-hepatitis liver cancer), genito-urinary (prostate, renal), skin (melanoma), head and neck, lung (adenocarcinoma, small cell, non-small cell), mesothelioma, hematological (leukemia, lymphoma, multiple myeloma), sarcoma, and germ cell tumors. Several different strategies have been used in an array of different tumor types.

Inserting tumor suppressor genes. Many tumors lack functional tumor suppressor genes. These genes code for proteins that can arrest tumor growth, and promote apoptosis of the tumor cells. The tumor suppressor gene most frequently tested in gene therapy trials has been the gene coding for p53. The p53 protein is able to arrest the cell cycle following DNA damage and is also involved in apoptosis. Efficient delivery and expression of the wild-type p53 gene has been shown to cause regression of established human tumors, prevent the growth of human cancer cells in culture or render malignant cells from human biopsies non-tumorigenic in nude mice. Some clinical trials using the p53 gene have been combined with standard therapeutic modalities such as chemotherapy and radiotherapy.

Immunotherapy. The basic precept underlying immunotherapy of cancer is that tumors possess antigens that elicit weak humoral and/or cellular reactions in tumor-bearing hosts. By intensifying the anti-tumor immune responses, tumors could be controlled or eradicated. Intensifying the immune response has been attempted by a number of different strategies including vaccination with tumor cells engineered to express immunostimulatory molecules, vaccination with recombinant viral vectors encoding tumor antigens, vaccination with dendritic cells expressing tumor antigens or tumor-derived RNA, naked DNA vaccines, and intratumoral injection of vectors encoding cytokines or major histocompatibility molecules.

Gene-directed enzyme prodrug therapy. Gene-directed enzyme prodrug therapy (GDEPT) constitutes introducing genes that encode enzymes capable of converting prodrugs to cytotoxic drugs. Non-toxic prodrugs can thus be administered in high doses with no untoward effects and converted in situ to the cytotoxic drug where it is needed (i.e., in the tumor and its immediate environment). This strategy constitutes using gene therapy to better utilize conventional chemotherapy. Several GDEPT systems have been used in clinical trials. The most commonly used system is HSV-thymidine kinase to convert the non-toxic prodrug ganciclovir into the cytotoxic triphosphate ganciclovir.

Liver Gene Therapy

The liver is a key organ for most metabolic pathways and therefore numerous metabolic inherited diseases have their origin in this organ. Two approaches are used for liver gene transfer: in vivo gene therapy, which is accomplished by delivery of vectors into the patient, and ex vivo, where cells are isolated from a resected liver lobe, genetically modified in vitro and then transplanted back into the recipient. Candidate diseases for liver gene therapy include primary liver diseases in which hepatocytes are injured and genetic defects altering a specific function of the hepatocyte but causing extrahepatic manifestations. The former category includes genetic disorders such as alpha 1-antitrypsin deficiency, type I tyrosinemia, Progressive Familial Intrahepatic Cholestasis type III or Wilson's disease. Accumulation of toxic products in hepatocytes leads to extensive hepatoxicity, and in such situations, healthy or corrected hepatocytes have a selective growth advantage over resident diseased hepatocytes. The latter category includes metabolic deficiencies, such as Crigler-Najjar syndrome type I, ornithine transcarbamylase (OTC) deficiency, type IIa familial hypercholesterolemia and coagulation defects such as hemophilia A and B and afibrinogenemia. Acquired hepatic diseases could also benefit from genetic approaches, such as viral hepatitis if hepatocytes could be made refractory to the replication of hepatitis B or C viruses, liver cancers if transgenes could trigger cell suicide, and fulminant liver failure if the liver could be protected from massive injury. Currently, orthotopic liver transplantation (OLT) is the only available therapy for end-stage liver diseases. Unfortunately, many patients still succumb while waiting for a donor organ (approximately 15%). An alternative to OLT is thus crucial for end-stage liver diseases.

The liver has unique features for in vivo and ex vivo gene therapy. It is the largest organ in the body and a highly vascularized organ. It is the only organ in the body to have two circulation systems, the systemic with the hepatic artery that brings oxygenated blood directly from the heart and the portal with the portal vein that brings nutrients from the gut and supplies 70% of the blood flow to the liver. In addition, it has a system of ducts that transports toxins out of the liver via bile into the small intestine, which is of importance for liver gene therapy applications since it allows hepatocytes to excrete bile salts, copper, bilirubin, etc, which cause liver diseases. The liver is divided into different segments based on the blood supply, which can be safely and individually removed (up to a 70% liver resection). About 70% of the liver cells are hepatocytes that are easily purified from the other cell types by differential sedimentation. Finally, but not the least, the liver is an organ with a very low cell-turn over (<1% dividing hepatocytes under normal conditions), but has the remarkable ability to massively regenerate following various types of injuries until it regains its original mass.

Gene Therapy of Liver Cancer

Gene therapy constitutes the transfer of genetic material to a patient with the aim to correct a disease. Gene delivery can be performed directly into the subject, using a variety of vehicles named vectors (in vivo gene therapy), or it can be done on isolated cells in vitro that are subsequently introduced into the organism (ex vivo gene therapy).

Cancer has been the main focus of gene therapy approaches for several reasons. First, the genetic alterations that contribute to the malignant transformation of cells are being unraveled with increasing detail in the last two decades, and this provides multiple candidate targets for gene therapy intervention. And second, the dismal prognosis of most patients with advanced cancers results in a desperate need for new therapeutic interventions and influences the risk-benefit balance that is key to clinical development of such a new platform.

Liver cancer is a good example of this situation. Hepatocellular carcinoma (HCC) accounts for 80% of primary liver tumors in adults; it has an increasing incidence and a poor 5-year survival rate of about 7% despite treatment. In addition, the liver is the most frequent site of metastasis, especially from gastrointestinal cancer. Potentially curative therapies such as liver transplantation and surgical resection can only be applied to a minority of subjects because of the advanced disease at the time of diagnosis and the lack of suitable organ donors. Other regional treatments may be beneficial for unresectable HCC, but local failure or recurrence is frequent and long term survival remains poor. Clinical trials performed so far have shown that side effects are acceptable in most of the cases, and the mechanism of action is different from standard treatments, so a combination may achieve a synergistic effect. Furthermore, the refinement of interventional therapies for HCC provides new possibilities for the delivery of gene therapy vectors into hepatic tumors, increasing the effective dose and minimizing potential side effects derived from nontarget cell transduction.

Restoration of tumor suppressor genes. This strategy is the most intuitive application of gene therapy for the treatment of HCC and other cancers. It is clear that the loss of function of certain genes is associated with malignant transformation of cells. Under experimental conditions, it has been shown that restoration of tumor suppressor genes can revert the malignant cell phenotype. However, therapeutic application of this observation faces various difficulties. Cancer cells often suffer some degree of genetic instability. When they lose their capacity to sense and repair damaged genes, mutations accumulate and cells with higher proliferation rate and lower sensitivity to apoptotic stimuli are selected sequentially. Under these circumstances, they may become insensitive to the restoration of a particular tumor suppressor gene.

Despite all these considerations, the transfer of p53 tumor suppressor gene has shown effect in several animal models of cancer, including HCC (Anderson Sc et al., Clin Cancer Res 1998, 4, 1649-59; Mitry R R et al., Hepatology 2000, 31, 885-9). This proof of concept has stimulated the use of p53 as a therapeutic gene. Mutations in p53 or alterations in its pathway have been described in more than 50% human cancers. When cells lack functional p53, they accumulate mutations that lead to malignant initiation, progression and resistance to treatments. Thus, the restoration of p53 may render tumor cells sensitive to apoptotic stimuli, even if they have accumulated other mutations. This may explain the therapeutic effect observed in pre-clinical models, and suggests a potential role of p53 as an adjuvant for conventional therapies that induce apoptosis in cancer cells.

Inhibition of oncogenes. Correction of the imbalance between positive and negative proliferation signals can be attempted by inhibiting the function of genes implicated in the maintenance of unrestricted cell proliferation and acquisition of metastatic phenotype. Hopefully, the inhibition of oncogene expression will not only decrease cell proliferation, but also restore sensitivity of cells to apoptotic stimuli. For instance, it is known that the inhibition of the Ras oncogene, apart from blocking a cascade of mitotic signals, relieves the repression exerted on the p53 pathway and predisposes cells to apoptosis (Halaschek-Wiener J et al., Cell Signal 2004, 16, 1319-27). This may be the case for other oncogenes such as the pituitary tumor transforming gene 1 (PTTG1) (Cho-Rok J et al., Hepatology 2006, 43, 1042-52). Another example is the catalytic subunit of telomerase (telomerase reverse transcriptase, TERT) (Saretzki G et al., Cancer Gene Ther 2001, 8, 827-34).

Different methods are used to inhibit expression of oncogenes. One of them is based on the transfer of antisense nucleotides, artificial sequences complementary to the mRNA corresponding to the gene whose inhibition is attempted. These can be short sequences (antisense oligonucleotides, ASO), or the full cDNA. Several mechanisms account for the blocking of gene expression, with the most widely spread and studied being the degradation of RNA-DNA hybrids by cell nucleases. A more recent approach is RNA interference, another posttranscriptional gene silencing mechanism based on the production of double-stranded stretches of RNA complementary to the target mRNA. Using the endogenous cell machinery, the double-stranded RNA is processed into short interfering RNAs (siRNAs) or microRNAs (miRNAs) that recognize the cognate mRNA and trigger its degradation, for the former, or arrest its translation, for the latter. Alternatively, the siRNAs or miRNAs can be transfected directly. In the "triple helix" strategy, the inhibitory oligonucleotides (triplex-forming oligonucleotides, TFOs) are targeted to the cellular double-stranded DNA. They interact with polypurine-polypyrimidine sequences in the minor or major grove of genomic DNA and block gene expression at different levels depending on the localization of the complementary sequence. They could be potentially used not only for gene expression modification, but also in gene correction strategies. Finally, the expression of secreted or intracellular antibody-based molecules has been proposed to block the function of oncogenes.

In the case of HCC, the inhibition of several genes has shown potential antitumor effect. Most reports provide proof of concept showing growth inhibition or induction of apoptosis using HCC-derived cell lines in cell culture. Studies in animal models show growth retardation in tumors, especially when cancer cells are transfected ex vivo, but complete eradication is difficult when in vivo gene therapy is tested on pre-existing tumors. Since telomerase and Wnt pathway activation are frequently associated with HCC, different approaches including antisense molecules and siRNA have been used to inhibit them (Liu S X et al., World J Gastroenterol 2004, 10, 366-70; Jiang Y et al., J Cancer Res Clin Oncol 2004, 130, 671-8; Sangkhathat S et al., Int J Oncol 2006, 28, 715-22). Antisense technology was also used against FGF-2 (Maret A et al., Cancer Res 1995, 55, 5075-9), VEGF (Gu S et al., World J Gastroenterol 2004, 10, 535-9) and COX-2 genes (Wang X H et al., World J Gastroenterol 2005, 11, 6110-4). The triplex helix approach showed similar results as antisense technology for the inhibition of IGF-I and induction of apoptosis in HCC cells (Upegui-Gonzalez L C et al., Hepatogastroenterology 2001, 48, 660-6). The inhibition of PTTG1 and urokinase-type plasminogen activator (u-PA) has been accomplished using siRNA on HCC cells (Salvi A et al., Mol Cancer Ther 2004, 3, 671-8). The p28-GANK oncoprotein, which induces hyperphosphorylation and increased degradation of pRB was found overexpressed in the majority of HCCs, and repeated administration of an adenoviral vector that induces the production of siRNA against p28-GANK caused a dramatic decrease in the growth of human HCC xenografts in nude mice (Li H et al., Gastroenterology 2005, 128, 2029-41).

Gene-directed enzyme/prodrug therapy (GDEPT). This approach is based on the transfer of exogenous genes that convert a non-toxic prodrug into a cytotoxic metabolite in cancer cells. Once the prodrug is administered systemically, transduced cells expressing the converting enzyme die and, in some cases, provoke the destruction of surrounding cells (bystander effect). Unlike other gene therapy strategies, GDEPT lacks intrinsic tumor specificity, and relies on tumor targeting at the levels of cell transfer (depending on the vectors and the route of administration) and gene expression (depending on tumor-specific promoters). The efficacy of a GDEPT system is highly influenced by the extent of the bystander effect, because the fraction of transduced cells in a tumor is generally low with current gene therapy vectors.

The thymidine kinase gene from HSV-1 (HSV-TK) used in conjunction with the prodrug ganciclovir (GCV) is the earliest and most used GDEPT system applied to HCC and other cancers (Fillat C et al., Curr Gene Ther 2003, 3, 13-26). It has shown significant antitumor effect in relevant animal models of HCC, such as carcinogen-induced HCC in rats (Qian C et al., Hum Gene Ther 1997, 8, 349-58). HSV-TK converts ganciclovir into the monophosphate intermediate that is subsequently transformed into the triphosphate form by cellular enzymes. Ganciclovir-triphosphate is incorporated into the DNA and causes apoptosis in a cell cycle-dependent manner. Apart from the therapeutic purpose, HSV-TK can be considered a reporter gene for PET analysis.

The yeast cytosine deaminase converts the antifungal drug 5-fluorocytosine (5-FC) into the cytotoxic thymidylate synthetase inhibitor 5-fluorouracil (5-FU) (Kievit E et al., Cancer Res 1999, 59, 1417-21). This metabolite can diffuse locally and cause wider bystander effect than phosphorylated ganciclovir, but the cytotoxicity is also cell cycle-dependent. The system has been used in animal models of primary and metastatic liver cancer with good results (Nyati M K et al., Gene Ther 2002, 9, 844-9; Zhang M et al., Cancer Res 2003, 63, 658-63). The efficacy of 5-FU on HCC patients is very low, but this strategy could achieve high local concentrations of the drug.

Other GDEPT approaches generate very potent DNA cross-linking agents whose effects are largely cell cycle-independent. These include the cytochrome P450/cyclophosphamide (Kan O et al., Expert Opin Biol Ther 2002, 2, 857-68) and the nitroreductase/dinitrobenzamide CB systems. Regarding the latter (Palmer D H et al., J Clin Oncol 2004, 22, 1546-52), intratumor administration of a first generation adenoviral vector expressing nitroreductase in HCC patients is safe and feasible. Transgene expression was dose-dependent and is supposed to be clinically relevant, although no prodrug was administered to patients in this study. Strong immune responses against the vector and the therapeutic gene were observed, indicating that re-administration of the treatment may not be beneficial. The antitumor effect and toxicity of this approach in patients receiving the prodrug requires new clinical trials.

An approach closely related to GDEPT constitutes the delivery of the sodium iodide symporter (NIS) gene to cancer cells (Kang J H et al., J Nucl Med 2004, 45, 1571-6). Since NIS is necessary for the internalization of $^{131}$I in the cell, a higher dose would be accumulated in cells expressing NIS, as it happens in thyrocytes, resulting in cell cycle blockade and death. Using this method, the extent and location of gene transfer can be detected by tomography. An adenovirus vector expressing NIS under the control of the CMV promoter has been used for the treatment of HCC in a model of chemically induced tumors in rats (Faivre J et al., Cancer Res 2004, 64, 8045-51). After injection of the vector in pre-existing nodules, specific accumulation of $^{131}$I and significant reduction in tumor volume was observed.

Targeted expression of cytotoxic/pro-apoptotic genes. This strategy is based on the selective transfer of genes that will cause the destruction of the cancer cells by different mechanisms. The concept is similar to GDEPT, but in this case the effect does not depend on any exogenous drugs. This can be an advantage in some circumstances, but on the other hand it lacks the possibility of modulating the cytotoxicity pharmacologically. This means that the system relies mostly on the targeting of gene transfer and expression into cancer cells, using specific surface ligands or promoters. The promoters for alpha-fetoprotein (AFP) and TERT have been used to control the expression of the diphtheria toxin fragment A and other cytotoxic genes in HCC cells, but the toxicity of these treatments on relevant animal models is unclear (Abdul-Ghani R et al., Mol Ther 2000, 2, 539-44; Kunitomi M et al., Jpn J Cancer Res 2000, 91, 343-50).

Figure 6:
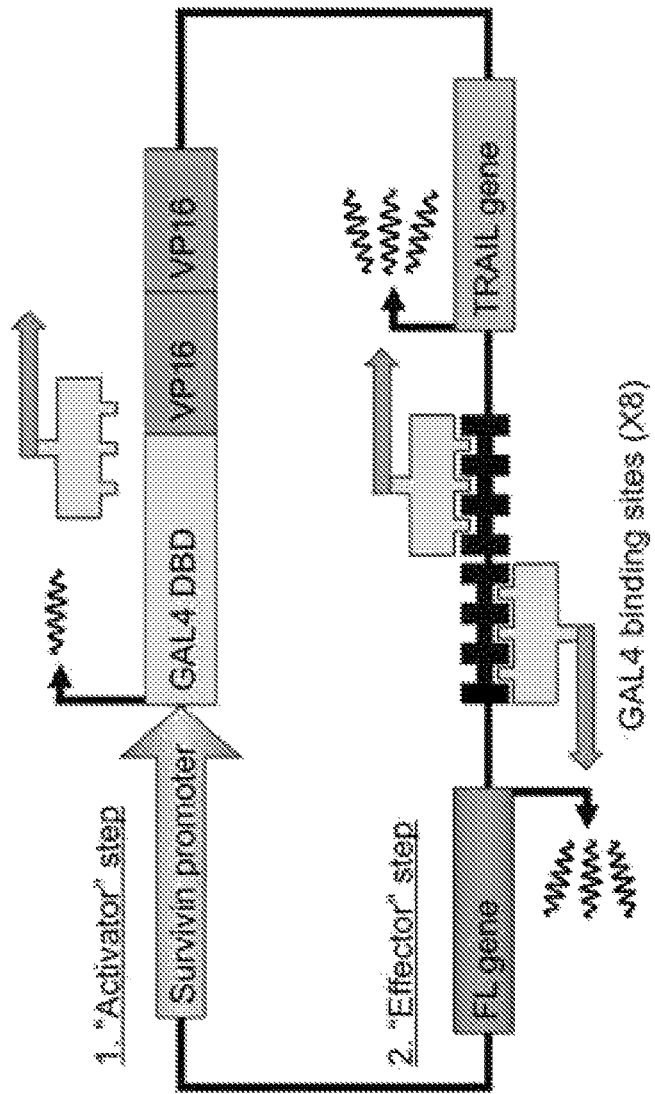
FIG. 6. Schematic diagram of the Survivin-targeted bi-directional two-step transcriptional amplification (TSTA) system.

Alternatively, the mechanism of action of the lethal gene can provide some tumor specificity. This is the case of tumor necrosis factor-related apoptosis-inducing ligand (TRAIL). Unlike other members of the TNF ligand family, such as FASL and TNF-alpha, TRAIL induces apoptosis preferentially of cancer cells and may have reduced heptotoxicity. The extracellular domain of TRAIL works as a soluble cytokine and induces apoptosis of cancer cells at distant locations from the producing cell. Recently, a bi-directional, two-step transcriptional amplification (TSTA) system driven by the tumor-specific Survivin promoter to amplify the correlated expression of both the reporter gene firefly luciferase (FL) and therapeutic gene TRAIL was shown to specifically target orthotopic tumors and avoid normal hepatocyte expression following systemic administration (Ahn B-C et al., Gene Ther 2011, 1-7). Referring to FIG. 6, in the first "activator" step of the system, the cancer-specific Survivin promoter drives the expression of the GAL4-VP16-2 fusion protein. GAL4-VP16-2 constitutes two tandem repeats of the N-terminal portion of the VP16 activation domain (aa 413-454) fused to the GAL4 DNA-binding domain (DBD; aa 1-147). In the second "effector" step of the system, the GAL4-VP16-2 fusion protein binds to GAL4-responsive minimal promoter and bi-directionally drives the expression of both the reporter gene (RG) FL and therapeutic gene (TG) TRAIL. The use of the GAL4-VP16-2 fusion protein leads to the amplification of both TG and RG simultaneously, whereas the tightly coupled FL allows indirect determination of both the location and level of TRAIL expression using bio-luminescence imaging.

Immunotherapy. Cytokines are key mediators in the function of the immune system. They have been extensively used to stimulate the immune response against tumors, including interleukins 2, 7, 12, 15, 18, 21, 23 and 24; interferon alpha, beta and gamma; tumor necrosis factor alpha; granulocyte-macrophage colony stimulating factor (GM-CSF), and others. Their effect on different cell components of the immune system and their influence on the expression of endogenous factors are extremely complex. Most of these cytokines do not have an intrinsic tumor-specific effect, but they may enhance the precarious immune response against tumors if the dose, location and timing are carefully controlled. For example, different animal models of HCC (Barajas M et al., Hepatology 2001, 33, 52-61; Waehler R et al., Hum Gene Ther 2005, 16, 307-17) and a phase I clinical trial in liver cancer patients (Sangro B et al., J Clin Oncol 2004, 22, 1389-97) have demonstrated the antitumor effect of a gene therapy vector expressing interleukin-12 (IL12).

The transfer of genes encoding tumor-specific antigens such as AFP has been used with the aim to break the immune tolerance against HCC (Grimm C F et al., Gastroenterology 2000, 119, 1104-12). The pre-clinical efficacy of this approach depends on the particular animal model employed (Saeki A et al., Int J Mol Med 2004, 13, 111-6), suggesting that high variability could be expected in patients. A different approach involves the administration of activated effector or antigen-loaded presenting cells to fight cancer. The efficacy of these cells can be increased if they are manipulated genetically to express antigens, cytokines or co-stimulatory molecules (ex vivo gene therapy). Syngeneic fibroblasts or cancer cells expressing IL12 (Peron J M et al., J Gastroenterol Hepatol 2004, 19, 388-96) or IL2 plus B7 (Ge N L et al., World J Gastroenterol 2003, 9, 2182-5) can trigger an immune response against HCC in murine models. However, the use of cancer cells as a source of antigens and cytokines poses obvious technical difficulties in the clinical setting. An attractive alternative is the use of autologous dendritic cells (DC), professional antigen presenting cells that express the co-stimulatory molecules (CD80, MHC class I and II, etc.) necessary for efficient activation of effector cells. DCs expressing AFP (Vollmer C M et al., Cancer Res 1999, 59, 3064-7), cytokines (Melero I et al., Gene Ther 1999, 6, 1779-84) or co-stimulatory molecules (Zhu M et al., Cancer Res 2001, 61, 3725-34) have been successfully used in animal models of HCC and gastrointestinal cancer (Tirapu I et al., Curr Gene Ther 2002, 2, 79-89). These results encouraged the initiation of a phase I clinical trial in which DCs expressing IL12 after ex vivo infection with an adenoviral vector were injected into the tumor mass (Mazzolini G et al., J Clin Oncol 2005, 23, 999-1010). If cells could be made able to migrate to lymph nodes rather than being sequestered into the tumor by local factors (Feijoo E et al., Int J Cancer 2005, 116, 275-81), an efficient activation of effector cells and the establishment of relevant antitumor immune responses might be observed.

Adoptive cell therapy involves the infusion of autologous T cells or killer cells that have been expanded and activated in vitro. In animal models, it has been demonstrated that T cell expansion occurs in vivo in tumor-bearing mice that were treated with IL12 (Mazzolini G et al., Hum Gene Ther 2000, 11, 113-25). The infusion of these cells has antitumor effect on recipient mice, in synergy with in vivo gene therapy by an adenoviral vector expressing IL12. This suggests that gene immunotherapy can be used in combination with adoptive T-cell therapy in order to increase the efficacy observed in clinical trials that used either strategy alone.

Anti-angiogenesis. Since tumor growth requires intense neo-vascularization, a series of approaches aimed to specifically block the cancer-induced formation of new vessels have been developed. Anti-angiogenic factors such as endostatin have been identified and have demonstrated the ability to inhibit tumor growth in vivo. Since HCC is known to be much vascularized, antiangiogenic therapies may have a strong therapeutic benefit (Hong S Y et al., World J Gastroenterol 2004, 10, 1191-7). Other anti-angiogenic approaches are focused on blocking the VEGF receptor, which is an important mediator of angiogenesis. This can be achieved by expressing the soluble form of VEGF receptor, which sequesters VEGF (Goldman C K et al., Proc Natl Acad Sci USA 1998, 95, 8795-800). The same approach has been used to block the endothelium-specific receptor Tie2, which affects direct tumor growth and neovascularization (Lin P et al., Proc Natl Acad Sci USA 1998, 95, 8829-34). The pigment epithelium derived factor (PEDF) has been recently discovered as an anti-angiogenic protein expressed in normal liver (Dawson D W et al., Science 1999, 285, 245-8) that is downregulated in HCC patients, suggesting a possible role in tumor progression. The transfer of PEDF has antitumor effects in a murine model of HCC (Matsumoto K et al., Hepatology 2004 40, 252-9). NK4 is a fragment of the hepatocyte growth factor (HGF) that acts as a HGF antagonist and blocks angiogenesis. The intrasplenic administration of an adenoviral vector expressing a secreted form of NK4 caused reduction in the vascularization and growth of pancreatic metastasis in the liver of mice (Murakami M et al., Int J Cancer 2005, 117, 160-5).

Gene Therapy for Inborn Errors of Liver Metabolism

Several different types of vectors, both viral and nonviral, have been developed for liver-directed gene therapy and have resulted in phenotypic correction in numerous animal disease models. The optimal vector for in vivo liver-directed gene therapy should be able to transfer genes to a high percentage of hepatocytes with limited toxicity. However, the available vectors have all shown some limitations (see Table). In aiming at the treatment of liver metabolic diseases an important issue is how much of the liver needs to be corrected (i.e., percentage of hepatocytes) to achieve clinically relevant improvements. The percentage of hepatocyte transduction required for phenotypic correction is generally low in non-cell autonomous disorders such as hemophilia A and B or mucopolysaccharidoses and higher in cell autonomous defects such as urea cycle disorders. As a general principle, maximizing therapeutic gene expression per cell and minimizing the vector dose for a clinical effect are desirable.

TABLE

Overview of Gene Therapy Vectors.

|  | Genetic material | Packaging capacity | Vector genome forms | Advantages | Disadvantages |
| --- | --- | --- | --- | --- | --- |
| Retrovirus | RNA | 8 kb | integrated | High efficiency integration, no viral immune response, long-term expression | Transduction only dividing cells, insertional carcinogenesis |
| Lentivirus | RNA | 8 kb | integrated | Non-dividing cells, long-term | Integration into active genes, risk |

TABLE-continued

Overview of Gene Therapy Vectors.

| | Genetic material | Packaging capacity | Vector genome forms | Advantages | Disadvantages |
|---|---|---|---|---|---|
| Adenovirus | dsDNA | Up to 35 kb | episomal | expression Non-dividing cells, large cloning capacity, high transduction levels, long-term expression | of replication competent HIV Acute toxicity |
| Adeno-associated vectors | ssDNA | 5-9 kb | episomal (>90%), integrated (<10%) | Non-dividing cells, long-term expression | Limited cloning capacity, CTL-mediated immune reaction |
| Naked plasmid DNA | dsDNA | unlimited | episomal | Non-dividing cells, no inflammatory response, large cloning capacity, long-term expression, ease preparation | Low efficiency of transduction, efficient and clinically relevant delivery method still to be developed |

Experimental gene therapy has been used to correct several metabolic diseases. We now describe two diseases, Crigler-Najjar syndrome type I and ornithine transcarbamylase deficiency (OTCD), as representative examples to illustrate the potential and the limitations of currently available strategies for liver-directed gene therapy.

Crigler-Najjar syndrome. Crigler-Najjar syndrome is an autosomal recessive condition characterized by non-hemolytic unconjugated hyperbilirubinaemia due to mutations in the gene encoding uridinediphosphoglucuronate glucuronosyltransferase (UGT1A1). Patients with Crigler-Najjar syndrome type I have life-threatening elevations of bilirubin. They are generally managed by phototherapy. Patients remain at risk of brain damage when intercurrent infections may increase production of bilirubin above that which can be controlled by phototherapy. Therefore, patients with Crigler-Najjar type I are often advised to consider liver transplantation, most frequently in the range of 18-25 years of age. Crigler-Najjar syndrome has long been considered a paradigm for developing gene therapies for metabolic liver diseases for several reasons: (a) the underlying defect is well characterized at the biochemical and molecular level; (b) the fraction of corrected hepatocytes required for clinical benefit is small, as deduced from hepatocyte transplantation studies; (c) the UGT1A1 does not require strict gene regulation for normal activity; (d) an animal model, the Gunn rat, recapitulating the human disease is available; (e) the outcome of the experimental therapies can be easily determined by measuring bilirubin fractions in serum and bile; (f) the UGT1A1 can be produced from skeletal muscle other than liver, its natural production site, and still retain the ability to transform bilirubin into water-soluble derivatives. For these several reasons, Crigler-Najjar syndrome type I is very attractive as a gene therapy disease candidate and its correction has been the goal of several studies using different vector systems. Retrovirus expressing UGT1A1 injected in newborns (Bellodi-Privato M et al., Hepatology 2005, 42, 431-8) or in conjunction with partial hepatectomy (Tada K et al., Liver Transpl Surg 1998, 4, 78-88) has achieved long-term correction of the hyperbilirubinemia in the Gunn rats. Lentivirus can also transduce nonproliferating cells and, in the Gunn rats, they resulted in stable reduction of bilirubin levels to near normal levels for over 1 year after treatment (van der Wegen P et al., Mol Ther 2006, 13, 374-81). Impressive lifelong correction of hyperbilirubinemia has been also reported in the Gunn rats following a single intravenous injection of helper-dependent adenoviral vector encoding UGT1A1 with negligible chronic toxicity (Toietta G et al., Proc Natl Acad Sci USA 2005, 102, 3930-5). Among different serotypes, adeno-associated virus serotype 1 was found to be the most efficient in correcting the hyperbilirubinemia of the Gunn rats although hepatic lesions were found in treated animals (Seppen J et al., Mol Ther 2006, 13, 1085-92). A reduction of hyperbilirubinemia has also been reported following hydrodynamic injection of naked plasmid DNA (Jia Z, Dankó I, Hum Gene Ther 2005, 16, 985-95). However, each of the vectors used in this disease model has some limitations which are currently preventing clinical applications.

Urea cycle disorders. Urea cycle disorders typically present in the first few days after birth with poor feeding, vomiting, lethargy, and coma due to hyperammonemia. Despite aggressive pharmacotherapy, patients are at high risk for repeated episodes of hyperammonemia and cumulative neurological morbidity and mortality. Given these significant problems, gene-replacement therapy could represent a viable alternative to orthotopic liver transplantation for long-term correction. Several studies over the past decade have found the therapeutic effect of several different first generation adenoviral vectors to be transient in the OTCD mouse models and lasting no longer than 2 months (Ye X et al., J Biol Chem 1996, 271, 3639-46). Helper-dependent adenoviral vector instead can mediate long-term correction of the OTCD animal model without chronic toxicity (Mian A et al., Mol Ther 2004, 10, 492-9; Brunetti-Pierri N et al., J Gene Med 2008, 10, 890-6). The new adeno-associated virus serotypes (AAV7, 8, 9), with higher efficiency of hepatocyte transduction, have also resulted in long-term phenotypic correction (Moscioni D et al., Mol Ther 2006, 14, 25-33).

Gene Therapy for Hemophilia

Hemophilia A (factor [F] VIII deficiency) has an incidence of ~1 in 5000 males, whereas hemophilia B (FIX deficiency) has an incidence of 1 in 25,000 to 30,000 males. As monogenic disorders, hemophilia A and B are compelling candidates for treatment with gene therapy. In hemophilia, a therapeutic benefit achieved by gene therapy should only require a modest increase (1%) in the endogenous factor level; response to treatment can be monitored easily; and there are relevant small and large animal models. The two main approaches aiming to restore factor VIII or factor IX production are based on genetically modified cells or direct in vivo gene delivery using viral or plasmid vectors.

Implantation of genetically modified, terminally differentiated cells. Palmer T D et al., Blood 1989, 73, 438-45 transduced mammalian fibroblasts with different retroviral vectors expressing the FIX gene. They observed transgene expression in vitro. They also demonstrated FIX production in rats and nude mice after implantation.

The first clinical trial of genetically modified, terminally differentiated cells was performed on patients in China (Qiu X et al., Chin Med J (Engl) 1996, 109, 832-9; Lu D R et al., Sci China B 1993, 36, 1342-51). Retroviral vectors were constructed to introduce human FIX into autologous primary skin fibroblasts, which were injected in multiple sites of the patients. The authors reported an increase in FIX expression and improvement of the bleeding phenotype.

Roth D A et al., N Engl J Med 2001, 344, 1735-42 developed an ex vivo method of nonviral transfer of the FVIII gene into cells from patients with severe hemophilia A. Fibroblasts obtained from a skin biopsy were transfected with a plasmid carrying the B domain-depleted form of FVIII. A genetically modified clone expressing FVIII was propagated and implanted into the patients via laparoscopy. Using a mouse model of the human FVIII gene, the investigators achieved FVIII activity of >5%. Human clinical trials, however, reported marginal benefit.

Implantation of genetically modified stem cells. Genetic modification and transplantation of hemopoietic stem cells (HSCs) offer a reasonable method to introduce the FVIII transgene into cells that are long-lived and undergo self-renewal and differentiation. To date, this approach requires pretreatment with a myeloablative or reduced-intensity conditioning regimen to allow stem cell engraftment. Successful expression at curative levels of human and porcine FVIII in the mouse model has been reported by several groups (Moayeri M et al., Mol Ther 2004, 10, 892-902; Ide L M et al., Blood 2007, 110, 2855-63; Moayeri M et al., Mol Ther 2005, 12, 1034-42).

Embryonic stem cells have been evaluated as a potential "cellular factory" for human FVIII. Tet-WT-FVIII embryonic stem cells were established by integrating full-length human FVIII cDNA under the control of the TET operator, which enabled FVIII transcription to be induced by doxycycline stimulation. FVIII was present in the supernatant of liver-like embryoid bodies but not in that of undifferentiated embryonic stem cells or hemopoietic-like embryoid bodies, although FVIII mRNA was detected in all conditions (Kasuda S et al., J Thromb Haemost 2008, 6, 1352-9).

Van Damme A et al., Haemophilia 2003, 9, 94-103 successfully transduced human bone marrow mesenchymal cells in vitro with a retroviral vector encoding human B domain-deleted FVIII. The mesenchymal cells were then injected intrasplenically into NOD-SCID mice. The authors observed long-term persistence of the cells in vivo with therapeutic plasma levels of FVIII.

Lin Y et al., Blood 2002, 99, 457-62 have proposed that engineered autologous blood outgrowth endothelial cells (BOECs) may provide an effective strategy to treat hemophilia A. Human BOECs were cultured, transfected with a plasmid vector containing FVIII cDNA, and administered intravenously into NOD-SCID mice. The levels of human FVIII correlated with dose of BOECs and increased over time.

Several groups have developed a new method of sequestering and protecting FVIII from inactivation while improving haemostasis (Yarovoi H V et al., Blood 2003, 102, 4006-13; Shi Q et al., J Clin Invest 2006, 116, 1974-82). Transgenic FVIII$^{null}$ mice expressing human B domain-deleted FVIII were created under the control of a megakaryocytic, lineage-specific promoter. FVIII expression within platelets restored hemostasis in hemophilia A mice.

In vivo gene addition therapy using integrating viral vectors. A retroviral vector designed to express the human FVIII gene was administered to hemophilia A dogs resulting in improvements in bleeding phenotype (Lothrop C et al., Mol Ther 2000, 5, S289). Powell J S et al., Blood. 2003, 102, 2038-45 reported a phase I dose escalation study in subjects with severe hemophilia A involving a peripheral intravenous infusion of retroviral vector carrying a B domain-deleted human FVIII gene. Unfortunately, the therapeutic effect was transient, with subjects showing a FVIII level above 1%, but the vector not being detected at the end of the study in any patients.

In murine models, intraperitoneal administration of HIV-1-based lentivirus containing the B domain-deleted FVIII cDNA transduced liver, spleen, blood, and bone marrow (Kootstra N A et al., Mol Ther 2003, 7, 623-31). Liver-directed gene transfer via the portal vein using a HIV-1-based lentiviral vector carrying human FVIII or FIX resulted in low levels (~1%) of factor expression (Park F et al., Blood 2000, 96, 1173-6). Preinfusion partial hepatectomy designed to enhance hepatocyte cell cycling resulted in a four- to sixfold rise in FIX expression.

Figure 7:
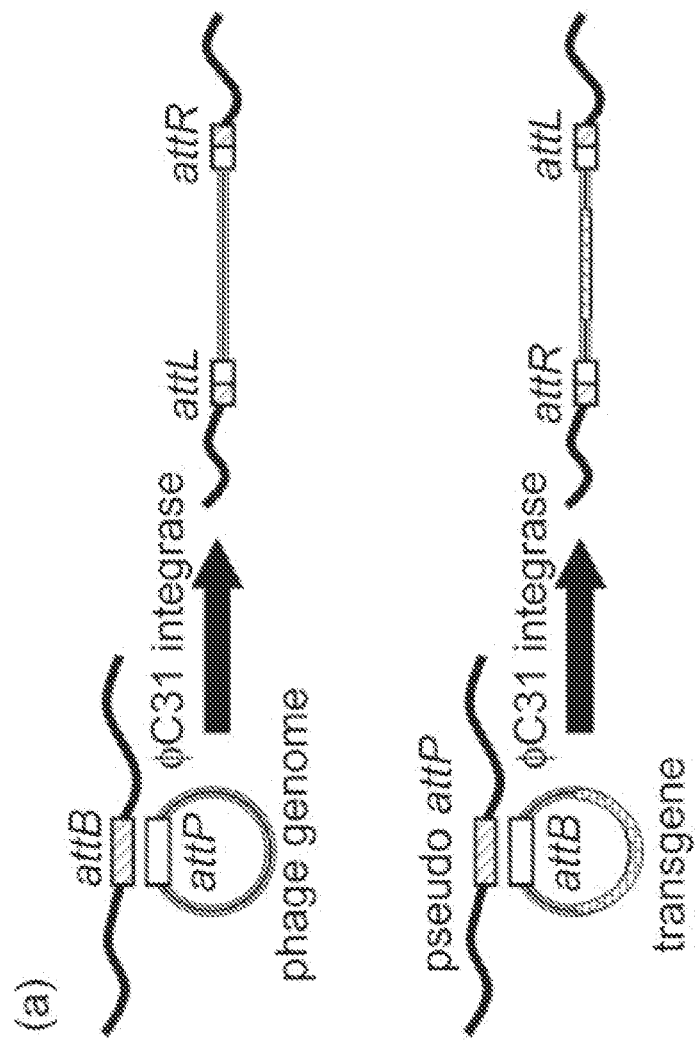
FIG. 7. Site-specific integration. In nature, ΦC31 integrase recombines the attP site in the phage genome with the attB locus of the *Streptomyces* genome. In the context of mammalian cells, ΦC31 integrase is used to mediate integration of a plasmid bearing attB and a transgene into native pseudo attP sites.

In vivo gene addition therapy using integrating plasmid vectors. Plasmids have been used to introduce FVIII and FIX in vivo in a murine model of hemophilia. In one study, supra-therapeutic levels of FVIII were observed after plasmid administration in hemophilia A mice (Ye P et al., Mol Ther 2004, 10, 117-26). Ye et al. of the Calos laboratory used plasmids to achieve site-specific FIX integration into murine hepatocytes (Olivares E C et al., Nat Biotechnol 2002, 20, 1124-8). Referring to FIG. 7, the bacteriophage C31 integrase was used to facilitate the insertion of plasmids containing an attB site into pseudo-attP sites in murine cells. The pseudo-attP sites had been previously shown to have enough identity with wild-type attP (found in the *Streptomyces* genome) to support integrase-mediated recombination. Hydrodynamic injection of the integrase and FIX bearing plasmid into the tail vein of the mouse resulted in normal plasma levels of human FIX that remained stable long term.

In vivo gene addition therapy using nonintegrating viral vectors. Early adenoviral vectors were associated with substantial toxicity, though subsequent modifications have improved their safety. First-generation adenoviral vectors were shown to produce therapeutic levels of FIX in rhesus macaques in dose-escalation studies but were associated with dose-limiting toxicities (Lozier J N et al., Blood 1999, 94, 3968-75). Dogs with FVIII deficiency exhibited a short-term correction upon administration of third-generation adenoviral vectors engineered to encode canine FVIII but developed hepatotoxicity (GalloPenn A M et al., Blood 2001, 97, 107-13).

Helper-dependent adenoviral vectors produced high-level, long-term transgene expression in vivo. In dogs with FVIII deficiency, a single injection of B domain-deleted canine FVIII resulted in short-term FVIII activity between 54% and 84% and long-term mitigation in the propensity to bleed (McCormack W M Jr et al., J Thromb Haemost 2006, 4, 1218-25). Here, the dose of vector required to achieve sustained expression was significantly greater than the dose tested on one human subject who suffered toxicity (Arruda V R, J Thromb Haemost 2006, 4, 1215-7).

The only human trial using an adenoviral vector enrolled a single human subject but was suspended due to unacceptable toxicity that was not predicted by mouse models. In both nonhemophilic and hemophilic mice (Balague C et al., Blood 2000, 95, 820-8), a single intravenous injection of a minimal adenovirus vector carrying the full-length hFVIII cDNA (Mini-AdFVIII) produced sustained expression of hFVIII at physiologic levels in both models, with correction of the bleeding phenotype. In the subsequent clinical trial, intravenous injection of the Mini-AdFVIII resulted in short-term expression of FVIII up to 3%, but transient hepatotoxicity resulted in suspension of the trial.

AAV vectors are limited by a small genetic payload capacity, thus constraining their use to the transfer of the small FIX gene or the modified FVIII gene (in the B domain-deleted form). Success has been demonstrated in both mouse and large animal models of hemophilia with long-term transgene expression. In these models, administration of the AAV vector was via multiple intramuscular injections or via liver-directed injection into the portal vein or hepatic artery.

AAV-1 and AAV-2 vectors expressing canine factor IX injected intramuscularly into immunodeficient (SCID) and immunocompetent (hemophilia B) mice have been successful (Chou H et al., Mol Ther 2001, 4, 217-22). Direct muscle injection of rAAV-human FIX in a hemophilia B dog resulted in expression of FIX in myocytes (Monahan P E et al., Gene Ther 1998, 5, 40-9). Sustained expression of canine FIX and partial correction of the bleeding phenotype has been achieved after administering AAV-canine FIX (Herzog R W et al., Nat Med 1999, 5, 56-63).

Liver-directed administration of AAV-human FIX achieved long-term therapeutic and, in some cases, curative levels of FIX in mouse models and modest levels in canines (Snyder R O et al., Nat Med 1999, 5, 64-70). Therapeutic expression of FVIII was achieved in dogs with hemophilia A using AAV-2-FVIII vector (Scallan C D et al., Blood 2003, 102, 2031-7). Sustained improvement of canine hemophilia B in animals has also been achieved (Mount J D et al., Blood 2002, 99, 2670-6).

Different AAV serotypes have been examined to improve transduction rates and reduce or avoid immunologic responses. AAV-8 and AAV-9 encapsidated vectors resulted in stable supraphysiologic human FIX levels in hemophilia B mice (Vandendriessche T et al., J Thromb Haemost 2007, 5, 16-24). Different AAV vector serotypes expressing canine FVIII administered to hemophilia A mice resulted in varying levels of transgene expression but the differences in large animals did not appear to be substantial (Jiang et al., Blood 2006, 108, 107-15).

Two trials have examined the use of AAV-2 vectors in human subjects. Manno C S et al., Blood 2003, 101, 2963-72 used an AAV-2 vector containing a modified FIX gene, which was administered via intramuscular injections in patients with severe hemophilia B. In one of the eight patients, expression of FIX after administration of AAV-2 vector was maintained for some years.

Manno C S et al., Nat Med 2006, 12, 342-7 infused an AAV-2 vector expressing human FIX via the hepatic artery in a dose-escalation trial in subjects with severe hemophilia B. The patients receiving a low dose showed no evidence of vector-related toxicity or of efficacy, with FIX levels remaining <1%. The patients receiving a higher dose showed transient expression of FIX, but this subsided and returned to an undetectable baseline apparently due to an immune response to AAV-2 from prior natural exposure. The use of different AAV serotypes has been proposed after evidence that AAV-2 is more likely to induce immunogenicity. Future trials will feature AAV-8 vectors instead of AAV-2 vectors, or immunosuppression, to reduce risk of an immune response.

Islet Neogenesis in the Liver

Recent studies support hepatocyte to islet cell reprogramming. There are multiple approaches to gene therapy for diabetes. One approach is the introduction of transcription or developmental factors to the liver to induce the production of insulin-producing cells in the liver. Kojima H et al., Nat Med 2003, 9, 596-603 showed that the helper-dependent adenoviral-mediated delivery of a combination of the Neurod and Btc genes to the liver induced islet neogenesis and reversed diabetes in STZ mice. The data indicate that Neurod-Btc gene therapy is a promising regimen to induce islet neogenesis for the treatment of insulin-dependent diabetes.

Example 1

Cell Culture and DNA Transfection. Morris hepatocellular carcinoma cells (hepatoma cells) were stably transfected with pRedShifted_Renilla_Luciferase DNA, phosphoglycerate kinase promoter, courtesy of the Gambhir laboratory, Stanford, Calif. (Loening A M et al., Nat Methods 2007, 4, 641-3), under neomycin selection using standard protocols. Coelenterazine H (Promega BioSciences, San Luis Obispo, Calif.) was used as a substrate for red-shifted-renilla luciferase (RSRL) to determine cell viability (Loening A M et al., Nat Methods 2007, 4, 641-3). For transfection experiments, hepatoma cells were seeded into a 96 well, black-wall plate ($10^4$ cells per well) in 100 µL of Glutamax culture medium (Invitrogen, Carlsbad, Calif.) without antibiotics and grown at 37 deg C. in a 5% CO2 atmosphere. After 12 hrs, Glutamax medium was exchanged with equal volumes of Opti-MEM (Invitrogen, Carlsbad, Calif.), for a total volume of 50 µL. For background and positive control transfection experiments, 50 µL of a transfection trial solution was used constituting 6 µL nonviral vector and 44 µL Opti-MEM. The nonviral vector included the plasmid DNA, pFLuc, courtesy of the Gambhir laboratory, Stanford, Calif. (Ray S et al., Mol Ther 2008, 16, 1848-56), encoding the firefly luciferase reporter gene under a CMV promoter. For bioluminescence (BLI) measurements of transfection efficiency, d-Luciferin (dLuc) signal was measured 24 hours post transfection using 50 µL of 3× dLuc reagent, 450 µg/mL (Invitrogen, Carlsbad, Calif.). Imaging of luciferase activity at 600 nm was performed using a Xenogen IVIS bioluminescent imager (CaliperLife Sciences, Hopkinton, Mass.). RSRL activity using coelenterazine H as substrate, 1 µg/mL, was measured at 480 nm to verify uniform protein expression and hepatoma cell viability. Background measurements were made using FuGene 6 (Roche, Indianapolis, Ind.) without pFLuc plasmid DNA. Fugene 6 was also used as a positive control per the manufacturer's protocol (6:1 m/v; 50 ng pFLuc plasmid DNA). Each measurement was made in triplicate.

For nonviral vector characterization experiments, a DNA stock solution (10 µL of desired concentration-0.05, 0.2, 0.5, or 2 mg/mL) and a 10 µL protamine sulfate stock solution using varied mass ratios of protamine sulfate to DNA [(P:D) (20:1, 50:1, 100:1, 200:1] were mixed together with manual agitation then incubated for 5 min at room temperature (RT). To this 20 µL solution, 10 µL of varying concentrations of iopamidol (Isovue®, Bracco Diagnostics, Princeton, N.J.) in Opti-MEM media were added (0%, 10%, 33%, 75%, 100%)

with or without 3x-ethiodized oil. This solution was then manually agitated and incubated for 20 min at RT. To this 30-µL solution, 1x-ethiodized oil in Opti-MEM media was added and mixed via iterative pipetting or using a 3-way metal stopcock for 16% ethiodized oil concentrations. 1x-ethiodized oil concentrations included 0, 1, 2, 4, 8, and 16%. The final nonviral vector transfection solution was 60 µL total volume. For each transfection, 6 µL of the final nonviral vector transfection solution was added to 44 µL of Opti-MEM per well of cells (50 µL final well volume). Log 10 signal was regressed on ethiodized oil concentration, the square of the ethiodized oil concentration, iopamidol concentration, and P:D ratio. All statistical analyses were done with Stata Release 9.2 (StataCorp LP, College Station, Tex.).

Nonviral vector gene delivery in hepatoma cells versus hepatocytes. The VIPER conditions affording efficient transfection relative to other conditions tested were selected for cell line comparison. DNA transfection of hepatocytes and hepatoma cells were compared as follows: protamine sulfate: DNA mass ratio of 50:1 and 33% iopamidol was kept constant while ethiodized oil (0, 2, 4%) and plasmid DNA mass (50 ng, 200 ng, 500 ng, 2000 ng) were varied. Nonviral transfection solutions and transfection efficiency measurements were performed as described above. Log 10 signal was regressed on ethiodized oil concentration, the square of the ethiodized oil concentration, DNA amount, and cell type. All statistical analyses were done with Stata Release 9.2 (StataCorp LP, College Station, Tex.)

Nonviral vector and Adenoviral Vector Comparison. Adenovirus encoding the fLuc gene (Ad5CMVfLuc) was obtained from the Gambhir laboratory (Ray S et al., Mol Ther 2008, 16, 1848-56) and amplified per established protocols. Gene transduction was measured (n=6) as described above for nonviral vector characterization. Ad5CMVfLuc was titrated ($10^{10}$, $10^{8}$, $10^{6}$, and $10^{4}$ plaque forming units, pfu, per 300 µL). A repeat measurement of transfection using VIPER (200 ng DNA; 50:1 P:DNA, 33% iopamidol, 2% ethiodized oil) was performed. Fugene 6 was used as a positive control (50 ng DNA; Fugene:DNA 6:1). Two cell lines analyzed included: hepatoma cells and hepatocytes. Log 10 signal was regressed on vector type and cell type. All statistical analyses were done with Stata Release 9.2 (StataCorp LP, College Station, Tex.).

Example 2

Intratumoral Gene Delivery in Rat Orthotopic Hepatic Tumors

Experiments begin with Morris hepatoma being implanted orthotopically into the liver of rats (van den Bosch M A et al., J Vasc Intery Radiol 2008, 19, S136-S137). Four nonviral gene transfer reagents are prepared by using the plasmid DNA, pFLuc, encoding the firefly luciferase reporter gene under a CMV promoter. The first reagent constitutes a DNA and protamine complex; the second, a DNA and protamine complex mixed with iopamidol and iodized oil; the third, a DNA and protamine complex mixed with iopamidol; and the fourth, a DNA and protamine complex mixed with iodized oil. Fourteen days after tumor implantation, gene delivery is performed by intratumoral administration. The rats undergo bioluminescence imaging (BLI) 24 hours post-gene delivery to evaluate gene expression. Expression is statistically analyzed for comparison between complexes by using the appropriate statistical test.

The results indicate that luciferase activity in the tumor is significantly higher for the group that receive DNA, protamine, iopamidol, and iodized oil than for any other group.

The conclusion is that it is feasible to use VIPER for the intratumoral transfection of plasmid DNA in experimentally induced orthotopic hepatic tumors.

Example 3

Intratumoral vs. Intravenous Gene Delivery in Rat Orthotopic Hepatic Tumors

Experiments begin with Morris hepatoma being implanted orthotopically into the liver of rats (van den Bosch M A et al., J Vasc Intery Radiol 2008, 19, S136-S137). A nonviral gene transfer reagent constituting a DNA and protamine complex mixed with iopamidol and iodized oil is prepared by using a plasmid DNA encoding the bacteriophage C31 integrase and a separate plasmid DNA carrying a bidirectional two-step transcriptional amplification system developed to amplify the weak transcriptional power of the cancer-specific survivin promoter, which drives the expression of both a therapeutic gene (tumor necrosis factor-α-related apoptosis-inducing ligand, TRAIL) and a reporter gene, firefly luciferase, appropriately engineered to support bacteriophage C31 integrase-mediated recombination. Fourteen days after tumor implantation, gene delivery is performed by intratumoral (IT) or intravenous (IV) administration. The rats undergo bioluminescence imaging (BLI) 24 hours post-gene delivery to evaluate gene expression and $^{18}$F-FDG positron emission tomography (PET) imaging on day 7 post-gene delivery to evaluate therapeutic efficacy. Expression and efficacy are statistically analyzed for comparison between delivery modes by using the appropriate statistical test.

The results indicate that BLI and PET are significantly higher for the group that receive IT administration than for the IV group.

The conclusion is that IT injection of VIPER demonstrates superior gene expression and therapeutic efficacy in experimentally induced orthotopic hepatic tumors.

Example 4

Intraarterial Gene Delivery in Rabbit Hepatic Tumors

Experiments begin with VX2 carcinoma being implanted into the liver of rabbits. Four nonviral gene transfer reagents are prepared by using the plasmid DNA, pFLuc, encoding the firefly luciferase reporter gene under a CMV promoter. The first reagent constitutes a DNA and protamine complex; the second, a DNA and protamine complex mixed with iopamidol and iodized oil; the third, a DNA and protamine complex mixed with iopamidol; and the fourth, a DNA and protamine complex mixed with iodized oil. Twenty days after tumor implantation, intraarterial gene delivery is performed by selective catheterization of the hepatic artery. Rabbits are euthanized 24 hours after gene delivery. Luciferase activity is assayed in the tumor and is statistically analyzed for comparison between complexes by using the appropriate statistical test.

The results indicate that luciferase activity in the tumor is significantly higher for the group that receive DNA, protamine, iopamidol, and iodized oil than for any other group.

The conclusion is that it is feasible to use VIPER for the intraarterial transfection of plasmid DNA in experimentally induced hepatic tumors.

Example 5

Transfection of Transformed Cells Derived from Other Tissues Besides Liver

VIPER was found to transfect 293T cells at the same efficiency as Morris cells. The nonviral reagent included the plasmid DNA, pFLuc, encoding the firefly luciferase reporter gene under a CMV promoter. 293T is a derivative of the 293 cell line into which the temperature sensitive gene for SV40 T-antigen was inserted. The 293 cell line is derived from human embryonic kidney cells. Morris cells are rat hepatoma cells.

Example 6

Comparable In Vivo Gene Delivery using VIPER Compared to a Cationic Lipid in Rat Orthotopic Hepatic Tumors Previously we have shown that a non-viral vector using combinations of iopamidol (I, iodinated contrast agent), protamine (P), and ethiodized oil (E), named VIPER, selectively transfects hepatoma cells. We hypothesized that intratumoral delivery to an orthotopic hepatocellular carcinoma (HCC) rat model would result in significant gene expression compared to a commercially available (although not clinically translatable) cationic lipid (Altogen).

Firefly luciferase plasmid DNA (F-Luc) was used as a reporter gene for gene delivery to a previously described orthotopic HCC rat model (van den Bosch M A et al., J Vasc Intery Radiol 2008, 19, S136-S137) using hepatoma cells (McARH7777). In vivo transfection efficiency was measured using a bioluminescence imaging CCD-camera. VIPER "cocktail" combinations optimized in vitro were used for intratumoral injection and compared to a cationic lipid (positive control) and naked DNA (negative control).

VIPER condition, 20:1 P:DNA, 8% E, 33% I, proved to have better transfection efficiency when compared to 50:1 P:DNA, 2% E, and 4% E combinations. The control cationic lipid proved to be 1.2-1.7× better than VIPER. Representative data include VIPER (20:1 P:DNA, 8% E, 33% I; n=3) $1.7 \times 10^5$ p/sec/cm$^2$/sr, VIPER (50:1 P:DNA, 2% E, 33% I; n=3) $1.2 \times 10^5$ p/sec/cm$^2$/sr, VIPER (100:1 P:DNA, 4% E, 33% I; n=3) $7.3 \times 10^4$, Altogen; n=4 $2.13 \times 10^5$ p/sec/cm$^2$/sr.

We have shown that the in vitro optimized VIPER combinations of ethiodized oil, protamine, iopamidol and DNA are translatable to in vivo gene delivery in an HCC rat model. Furthermore, transfection efficiency is comparable to a cationic lipid vector, albeit slightly less effective. In contrast to viral and cationic lipid vectors, VIPER (components of which are all FDA-approved) lends itself to iterative therapy and therefore a more easily translatable gene delivery strategy.

These examples and embodiments are illustrative and are not to be read as limiting the scope of the invention as it is defined by this specification and the appended claims.

All references cited in this specification are incorporated herein by reference.

What is claimed is:

1. A nonviral gene delivery vector comprising iopamidol, protamine, and ethiodized oil, wherein the concentration of ethiodized oil is between 1% and 8% and the concentration of iopamidol is between 10% and 33.

2. A drug product comprising a nonviral gene delivery vector consisting of plasmid DNA, iopamidol, protamine, and ethiodized oil, wherein the concentration of ethiodized oil is between 1% and 8% and the concentration of iopamidol is between 10% and 33.

3. The vector of claim 1 further comprising plasmid DNA.

4. The vector of claim 1 further comprising short interfering RNAs (siRNAs), microRNAs (miRNAs), antisense oligonucleotides (ASO), ribozymes, or triplex-forming oligonucleotides.

5. The vector of claim 3, wherein the protamine and DNA form a complex having a protamine to DNA mass ratio of between 1:1 to 1000:1.

6. The vector of claim 2, wherein the protamine and DNA form a complex having a protamine to DNA mass ratio of between 1:1 to 1000:1.

7. The vector of claim 2, wherein the amount of plasmid DNA is between 1 ng and 4000 ng.

8. The vector of claim 3, wherein the amount of plasmid DNA is between 1 ng and 4000 ng.

9. The vector of claim 2, wherein the plasmid DNA comprises a tumor suppressor gene, encodes a tumor-specific antigen, encodes an enzyme capable of converting a prodrug to a cytotoxic drug, comprises a cytotoxic or pro-apoptotic gene, encodes a cytokine, encodes an anti-angiogenic factor, encodes UGT1A1, encodes ornithine transcarbamylase, encodes factor VIII, encodes factor IX, or comprises a combination of the Neurod and Btc genes.

10. A process for transfecting mammalian cells comprising administering the vector of any of claim 1 to 3 to mammalian cells in an amount effective to transfect the cells.

11. The process of claim 10, wherein delivery is in vivo.

12. The process of claim 10, wherein delivery is in vitro.

13. The process of claim 10, wherein the cells are hepatoma cells.

14. The process of claim 10, wherein delivery is systemic.

15. The process of claim 10, wherein delivery is direct.

16. A process for making the nonviral gene delivery vector of claim 1 comprising mixing a DNA stock solution with a protamine solution, adding iopamidol, and adding ethiodized oil in amounts effective to make the nonviral gene delivery vector.

17. The vector of claim 3, wherein the plasmid DNA comprises a tumor suppressor gene, encodes a tumor-specific antigen, encodes an enzyme capable of converting a prodrug to a cytotoxic drug, comprises a cytotoxic or pro-apoptotic gene, encodes a cytokine, encodes an anti-angiogenic factor, encodes UGT1A1, encodes ornithine transcarbamylase, encodes factor VIII, encodes factor IX, or comprises a combination of the Neurod and Btc genes.

18. The vector of claim 3, wherein the protamine and DNA form a complex having a protamine to DNA mass ratio of between 50:1 and 200:1 and the concentration of ethiodized oil is between 2% and 4%.

19. The vector of claim 18, wherein the protamine and DNA form a complex having a protamine to DNA mass ratio of 50:1, the concentration of ethiodized oil is 2%, and the concentration of iopamidol is 33%.

* * * * *